(12) United States Patent
Botha-Oberholster et al.

(10) Patent No.: US 11,944,102 B2
(45) Date of Patent: Apr. 2, 2024

(54) METHOD FOR CONTROLLING PEST INFESTATIONS

(71) Applicant: Stellenbosch University, Stellenbosch (ZA)

(72) Inventors: Anna-Maria Botha-Oberholster, Stellenbosch (ZA); Hendrik Willem Swiegers, Stellenbosch (ZA); Nicolaas Francois Visser Burger, Somerset West (ZA)

(73) Assignee: Stellenbosch University, Stellenbosch (ZA)

( * ) Notice: Subject to any disclaimer, the term of this patent is extended or adjusted under 35 U.S.C. 154(b) by 784 days.

(21) Appl. No.: 15/733,580

(22) PCT Filed: Mar. 5, 2019

(86) PCT No.: PCT/IB2019/051768
§ 371 (c)(1),
(2) Date: Sep. 3, 2020

(87) PCT Pub. No.: WO2019/171272
PCT Pub. Date: Sep. 12, 2019

(65) Prior Publication Data
US 2021/0000124 A1 Jan. 7, 2021

(30) Foreign Application Priority Data
Mar. 5, 2018 (ZA) .................................. 2018/01488

(51) Int. Cl.
*A01N 63/60* (2020.01)
*C12N 15/113* (2010.01)

(52) U.S. Cl.
CPC ............ *A01N 63/60* (2020.01); *C12N 15/113* (2013.01)

(58) Field of Classification Search
CPC .......................... C12N 15/113; C12N 15/8286; Y02A 40/146; A01N 63/60
See application file for complete search history.

(56) References Cited

U.S. PATENT DOCUMENTS

2016/0053259 A1    2/2016  Puterka et al.

FOREIGN PATENT DOCUMENTS

WO    WO-2012078949 A2 *  6/2012  ........... C12N 15/113

OTHER PUBLICATIONS

Dombrovsky, Aviv et al.: "Characterization of RR-1 and RR-2 cuticular proteins from Myzus persicae", Comparative Biochemistry and Physiology Part B: Biochemistry and Molecular Biology, Elsevier, Amsterdam, NL, vol. 146, No. 2, Nov. 25, 2006 (Nov. 25, 2006), pp. 256-264, XP005873171, ISSN: 1096-4959, DOI: 10.1016/J.CBPB.2006.11.013.

(Continued)

*Primary Examiner* — J. E. Angell
*Assistant Examiner* — Keyur A Vyas
(74) *Attorney, Agent, or Firm* — Ryan L. Marshall; Barnes & Thornburg LLP

(57) ABSTRACT

The invention provides siRNA molecules for use in controlling pest infestation. The siRNA molecules target the mature mRNA of *D. noxia* cprr1-8 in a region between nucleotides 464 and 774 of SEQ ID NO: 23, or an equivalent region of an ortholog of *D. noxia* cprr1-8. Ingestion of the siRNA molecule by a pest inhibits the biological activity of the pest. In one embodiment, the siRNA molecule comprises a polynucleotide which has at least 80% sequence identity to the sequence 5' UAAACAAUCGCAAGAAGCUGA 3' (SEQ ID NO: 1) and a polynucleotide which has at least 80% sequence identity to the sequence 5' AGCUUC-UUGCGAUUGUUUAAG 3' (SEQ ID NO: 2). Compositions comprising the siRNA molecules, vectors encoding the (Continued)

siRNA molecules, and methods for using the siRNA molecules are also provided.

20 Claims, 18 Drawing Sheets

Specification includes a Sequence Listing.

(56) References Cited

OTHER PUBLICATIONS

Nicholson, Scott J. et al.: "The genome of Diuraphis noxia, a global aphid pest of small grains", BMC Genomics, vol. 16, No. 1, Jun. 5, 2015 (Jun. 5, 2015), XP55594360, DOI: 10.1186/s12864-015-1525-1.

Noh, Mi Young et al.: "Tribolium castaneum RR-1 Cuticular Protein TcCPR4 is Required for Formation of Pore Canals in Rigid Cuticle", Plos Genetics, vol. 11, No. 2, Feb. 9, 2015, p. e1004963, XP55593421, DOI: 10.1371/journal.pgen.1004963.

Swiegers, Hendrik et al.: "Silencing of Diuraphis noxia virulence gene through RNA interference using a novel siRNA delivery method", HPIS 2017 Hemipteran-Plant Interactions Symposium, Jun. 2017, XP55593393, Madrid, Spain. Retrieved from the Internet: URL: http://www.hpis2017.csic.es/wp-content/uploads/2015/12/Book_of_Abstracts_Hpis_2017_L.pdf [retrieved on Jun. 3, 2019] p. 205.

Swiegers, Hendrik et al.: "Silencing of Diuraphis noxia virulence gene through RNA interference using a novel siRNA delivery", Proceedings 13th International Wheat Genetics Symposium, Apr. 23-28, 2017, Tulln-Austria, Apr. 23-28, 2017, XP55593395, At ISBN: 978-3-900932-48-0 p. 296-297.

Visser, Ilze: "RNAi of selected insect genes. Thesis presented in fulfilment of the requirements for the degree Magister Scientiae", Dec. 2016, XP55593375, Retrieved from the Internet: URL: https://pdfs.semanticscholar.org/66d9/cb14e70eecf3acd0aec6a876aee637baeb9f.pdf [retrieved on Jun. 6, 2019].

Xiudao, Yu et al.: "Engineering plants for aphid resistance: current status and future perspectives", Theoretical and Applied Genetics; International Journal of Plant Breeding Research, Springer, Berlin, DE, vol. 127, No. 10, Aug. 24, 2014 (Aug. 24, 2014), pp. 2065-2083, XP035399808, ISSN: 0040-5752, DOI: 10.1007/S00122-014-2371-2 [retrieved on Aug. 24, 2014].

* cited by examiner

```
SA1_Sanger_DNA      ------------------------------------GGTATACGTCCAAAAAAATCACCATGAACA
SAM_NGS             CATCCCAACATACGGCAATTTTCTGATCACGGTATACGTCCAAAAAAATCACCATGAACA
                                                        ****************************

SA1_Sanger_DNA      CTTTGGTGAGTTAAATAATATTTCTTTAAATCTTCTTAAAAAGACATAGCAATATTATC
SAM_NGS             CTTTGGTGAGTTAAATAATATTTCTTTAAATCTTCTTAAAAAGACATAGCAATATTATC
                    ************************************************************

SA1_Sanger_DNA      ATTTTATTTTTAATTTAGTTATACAACGCATTGTATAATAGTTTCAATTTATAAACAGT
SAM_NGS             ATTTTATTTTTAATTTAGTTATACAACGCATTGTATAATAGTTTCAATTTATAAACAGT
                    ************************************************************

SA1_Sanger_DNA      TTAATTTAAAGAAAAAATAGTATARTTACTGAAATTATTTATTATTTTCGTACTTTATCA
SAM_NGS             TTAA--------------------------------------------------------
                    ****

SA1_Sanger_DNA      TACACTTATGAATTTTTAGTATTTTTGGTATACGAGAATATCTTATTATTTTATAAATAT
SAM_NGS             ------------------------------------------------------------

SA1_Sanger_DNA      CTTATAAAATAAATGCTCATATTATGTTATACTTATTTTTTAAATTAATGAAACTACGAA
SAM_NGS             ------------------------------------------------------------

SA1_Sanger_DNA      AAAATTAATTTTAACTCAAATTTTCAAATTTTTTAAGTTCAAATAAGTACCTCAATTTAT
SAM_NGS             ------------------------------------------------------------

SA1_Sanger_DNA      ATTATGAACAGTGTAAAAGTATAATATTTACGTTTACTGCAACCATTATTATATTAGAAT
SAM_NGS             ------------------------------------------------------------

SA1_Sanger_DNA      CAGTCTTATTATTTTTGTACTTCATAAAAAAATGCCTGAAAATTAAAATTTAAAAGATAT
SAM_NGS             ------------------------------------------------------------

SA1_Sanger_DNA      CTCTACAATTTAACGCATAGGTAATCTTATTAATCGTAATCATATTTTAACCAAATCCAT
SAM_NGS             ---------TTAACGCATAGGTAATCTTATTAATCGTAATCATATTTTAACCAAATCCAT
                             ***************************************************

SA1_Sanger_DNA      ATTTTAGTTTCAATTTAAAATTGACATTACACCTGTAAAAGTTTTCACAGTATATC---
SAM_NGS             ATTTTAGTTTCAATTTAAAATTGACATTACACCTGTAAAAGTTTTCACAGTATATCTTC
                    ********************************************************

SA1_Sanger_DNA      ------------------------------------TTCACAGCAAAAAATATGCATA
SAM_NGS             ACAGCAAAAAATATGCATAAAATTATTTCTTDCATGATTTCACAGCAAAAAATATGCATA
                                                        **********************

SA1_Sanger_DNA      AAATTATTTCTTTCCTCAGCACTTTATACAATTTTCGTGCCTTCGTTTTTAGGTAGTGTT
SAM_NGS             AAATTATTTCTTTCCTCAGCACTTTATACAATTTTCGTGCCTTCGTTTTTAGGTAGTGTT
                    ************************************************************

SA1_Sanger_DNA      AGTAGCTGTCATCGCAGCGGTGTCTGCTGCGGCCCCACCTCAGGAAGCTGCCAAAGCTTT
SAM_NGS             AGTAGCTGTCATCGCAGCGGTGTCTGCTGCGGCCCCACCTCAGGAAGCTGCCAAAGCTTT
                    ************************************************************

SA1_Sanger_DNA      TACTTTCAGTGGATTCCCATCCAACCAAGCCTACTACCCAGGCCAACAAGGGTACTACCC
SAM_NGS             TACTTTCAGTGGATTCCCATCCAACCAAGCCTACTACCCAGGCCAACAAGGGTACTACCC
                    ************************************************************
```

Figure 1a

```
SA1_Sanger_DNA    AGGATACATTGGTTACCAGGGTTATCAAGGTTACAGCGGATTCCGTAATGGATACTACCC
SAM_NGS           AGGATACATTGGTTACCAGGGTTATCAAGGTTACAGCGGATTCCGTAATGGATACTACCC
                  ************************************************************

SA1_Sanger_DNA    GGGACAACAAGGATACTACCCAGGATACCAAGGTTACCAGGGATACTACCCAGGATACCA
SAM_NGS           GGGACAACAAGGATACTACCCAGGATACCAAGGTTACCAGGGATACTACCCAGGATACCA
                  ************************************************************

SA1_Sanger_DNA    AGGTTACCAGGGATACTACCCAGGATATCAAGGTTTAATTTCGTTAATTATACGTCTAAA
SAM_NGS           AGGTTACCAGGGATACTACCCAGGATATCAAGGTTTAATTTCGTTAATTATACGTCTAAA
                  ************************************************************

SA1_Sanger_DNA    ACACTGCAGAGTCACATGATGTGTTATAAGTTTCTTATAATTTACTATTTTCACATAGGT
SAM_NGS           ACACTGCAGAGTCACATGATGTGTTATAAGTTTCTTATAATTTACTATTTTCACATAGGT
                  ************************************************************

SA1_Sanger_DNA    TACAACCGCGGTTACTACCCAGGTGCCCCAGCCGTCTACCCCACCGTCACCCCCGCCCCA
SAM_NGS           TACAACCGCGGTTACTACCCAGGTGCCCCAGCCGTCTACCCCACCGTCACCCCCGCCCCA
                  ************************************************************

SA1_Sanger_DNA    ATCATCGCACCAGTGCCAGTCGCGCCCAAGGCTGTTTCTCCAGTGTACAAACCCGTAGAC
SAM_NGS           ATCATCGCACCAGTGCCAGTCGCGCCCAAGGCTGTTTCTCCAGTGTACAAACCCGTAGAC
                  ************************************************************

SA1_Sanger_DNA    AACAAAGTGCCAGCTATCCTTAAACAATCGCAAGAAGCTGACTTGAACGGATTCAAATAC
SAM_NGS           AACAAAGTGCCAGCTATCCTTAAACAATCGCAAGAAGCTGACTTGAACGGATTCAAATAC
                  ************************************************************

SA1_Sanger_DNA    GGGTTAGTATTATAATTGGTACATTATTATTCGATCGGTTTTCTGCATCACAGCGAATGG
SAM_NGS           GGGTTAGTATTATAATTGGTACATTATTATTCGATCGGTTTTCTGCATCACAGCGAATGG
                  ************************************************************

SA1_Sanger_DNA    YGGATTAAAATTGAGAAATAGAGACCCGCGCCAAATGGCATGTCCACAAAAAATACATTG
SAM_NGS           TGGATTAAAATTGAGAAATAGAGACCCGCGCCAAATGGCATGTCCACAAAAAATACATTG
                   ***********************************************************

SA1_Sanger_DNA    TTTGTAAATAACGGATATATTTGTGTGCATTTTCAGATACGAAACCGAAAACGGCATCGT
SAM_NGS           TTTGTAAATAACGGATATATTTGTGTGCATTTTCAGATACGAAACCGAAAACGGCATCGT
                  ************************************************************

SA1_Sanger_DNA    CGCCCAGGCTGCTGGATACGTTAAGAACGCCGGTTCCGAAAACGCCGTCCAAGTGATCGA
SAM_NGS           CGCCCAGGCTGCTGGATACGTTAAGAACGCCGGTTCCGAAAACGCCGTCCAAGTGATCGA
                  ************************************************************

SA1_Sanger_DNA    AGGCTCGTATGCCTACATCGGTGACGATGGTGCTCCAGTCGAAGTCAAGTACTACGCTGA
SAM_NGS           AGGCTCGTATGCCTACATCGGTGACGATGGTGCTCCAGTCGAAGTCAAGTACTACGCTGA
                  ************************************************************

SA1_Sanger_DNA    CGAGACCGGTTACCACGCAGCCGGAAACGTCGTCCCGACCACTCCCCCAGAGATCGCCAA
SAM_NGS           CGAGACCGGTTACCACGCAGCCGGAAACGTCGTCCCGACCACTCCCCCAGAGATCGCCAA
                  ************************************************************

SA1_Sanger_DNA    GTCTTTGGAATTAATCGCCTCCCAACCACAGAAACCAGAAGACTCCAAAAAGAA------
SAM_NGS           GTCTTTGGAATTAATCGCCTCCCAACCACAGAAACCAGAAGACTCCAAAAAGAAGTAAAC
                  *****************************************************
```

Figure 1b

```
SAM_Sanger_DNA    ------------------------------CGGTATACGTCCAAAAAAATCACCATGAACA
SAM_NGS           CATCCCAACATACGGCAATTTTCTGATCACGGTATACGTCCAAAAAAATCACCATGAACA
                                                ****************************

SAM_Sanger_DNA    CTTTGGTGAGTTAAATAATATTTCTTTAAATCTTCTTAAAAAAGACATAGCAATATTATC
SAM_NGS           CTTTGGTGAGTTAAATAATATTTCTTTAAATCTTCTTAAAAAAGACATAGCAATATTATC
                  ************************************************************

SAM_Sanger_DNA    ATTTTATTTTTAATTTAGTTATACAACGCATTGTATAATAGTTTCAATTTATAAACAGT
SAM_NGS           ATTTTATTTTTAATTTAGTTATACAACGCATTGTATAATAGTTTCAATTTATAAACAGT
                  ***********************************************************

SAM_Sanger_DNA    TTAATTTAAAGAAAAAATAGTATARTTACTGAAATTATTTATTATTTTCGTACTTTATCA
SAM_NGS           TTAA--------------------------------------------------------
                  ****

SAM_Sanger_DNA    TACACTTATGAATTTTTAGTATTTTTGGTATACGAGAATATCTTATTATTTTATAAATAT
SAM_NGS           ------------------------------------------------------------

SAM_Sanger_DNA    CTTATAAAATAAATGCTCATATTATGTTATACTTATTTTTTAAATTAATGAAACTACGAA
SAM_NGS           ------------------------------------------------------------

SAM_Sanger_DNA    AAAATTAATTTTAACTCAAATTTTCAAATTTTTTAAGTTCAAATAAGTACCTCAATTTAT
SAM_NGS           ------------------------------------------------------------

SAM_Sanger_DNA    ATTATGAACAGTGTAAAAGTATAATATTTACGTTTACTGCAACCATTATTATATTAGAAT
SAM_NGS           ------------------------------------------------------------

SAM_Sanger_DNA    CAGTCTTATTATTTTTGTACTTCATAAAAAAATGCCTGAAAATTAAAATTTAAAAGATAT
SAM_NGS           ------------------------------------------------------------

SAM_Sanger_DNA    CTCTACAATTTAACGCATAGGTAATCTTATTAATCGTAATCATATTTTAACCAAATCCAT
SAM_NGS           ---------TTAACGCATAGGTAATCTTATTAATCGTAATCATATTTTAACCAAATCCAT
                           *************************************************

SAM_Sanger_DNA    ATTTTTAGTTTCAATTTAAAATTGACATTACACCTGTAAAAGTTTTCACAGTATATC----
SAM_NGS           ATTTTTAGTTTCAATTTAAAATTGACATTACACCTGTAAAAGTTTTCACAGTATATCTTC
                  ********************************************************

SAM_Sanger_DNA    ------------------------------------TTCACAGCAAAAAATATGCATA
SAM_NGS           ACAGCAAAAAATATGCATAAAATTATTTCTTDCATGATTTCACAGCAAAAAATATGCATA
                                                      **********************

SAM_Sanger_DNA    AAATTATTTCTTTCCTCAGCACTTTATACAATTTTCGTGCCTTCGTTTTTAGGTAGTGTT
SAM_NGS           AAATTATTTCTTTCCTCAGCACTTTATACAATTTTCGTGCCTTCGTTTTTAGGTAGTGTT
                  ************************************************************

SAM_Sanger_DNA    AGTAGCTGTCATCGCAGCGGTGTCTGCTGCGGCCCCACCTCAGGAAGCTGCCAAAGCTTT
SAM_NGS           AGTAGCTGTCATCGCAGCGGTGTCTGCTGCGGCCCCACCTCAGGAAGCTGCCAAAGCTTT
                  ************************************************************

SAM_Sanger_DNA    TACTTTCAGTGGATTCCCATCCAACCAAGCCTACTACCCAGGCCAACAAGGGTACTACCC
SAM_NGS           TACTTTCAGTGGATTCCCATCCAACCAAGCCTACTACCCAGGCCAACAAGGGTACTACCC
                  ************************************************************
```

Figure 2a

```
SAM_Sanger_DNA    AGGATACATTGGTTACCAGKGTTATCAAGGTTACAGCGGATTCCGTAATGGATACTACCC
SAM_NGS           AGGATACATTGGTTACCAGGGTTATCAAGGTTACAGCGGATTCCGTAATGGATACTACCC
                  ****************** *****************************************

SAM_Sanger_DNA    GGGACAACAAGGATACTACCCAGGATACCAAGGTTACCAGGGATACTACCCAGGATACCA
SAM_NGS           GGGACAACAAGGATACTACCCAGGATACCAAGGTTACCAGGGATACTACCCAGGATACCA
                  ************************************************************

SAM_Sanger_DNA    AGGTTACCAGGGATACTACCCAGGATATCAAGGTTTAATTTCGTTAATTATACGTCTAAA
SAM_NGS           AGGTTACCAGGGATACTACCCAGGATATCAAGGTTTAATTTCGTTAATTATACGTCTAAA
                  ************************************************************

SAM_Sanger_DNA    ACACTGCAGAGTCACATGATGTGTTATAAGTTTCTTATAATTTACTATTTTCACATAGGT
SAM_NGS           ACACTGCAGAGTCACATGATGTGTTATAAGTTTCTTATAATTTACTATTTTCACATAGGT
                  ************************************************************

SAM_Sanger_DNA    TACAACCGCGGTTACTACCCAGGTGCCCCAGCCGTCTACCCCACCGTCACCCCCGCCCCA
SAM_NGS           TACAACCGCGGTTACTACCCAGGTGCCCCAGCCGTCTACCCCACCGTCACCCCCGCCCCA
                  ************************************************************

SAM_Sanger_DNA    ATCATCGCACCAGTGCCAGTCGCGCCCAAGGCTGTTTCTCCAGTGTACAAACCCGTAGAC
SAM_NGS           ATCATCGCACCAGTGCCAGTCGCGCCCAAGGCTGTTTCTCCAGTGTACAAACCCGTAGAC
                  ************************************************************

SAM_Sanger_DNA    AACAAAGTGCCAGCTATCCTTAAACAATCGCAAGAAGCTGACTTGAACGGATTCAAATAC
SAM_NGS           AACAAAGTGCCAGCTATCCTTAAACAATCGCAAGAAGCTGACTTGAACGGATTCAAATAC
                  ************************************************************

SAM_Sanger_DNA    GGGTTAGTATTATAATTGGTACATTATTATTCGATCGGTTTTCTGCATCACAGCGAATGG
SAM_NGS           GGGTTAGTATTATAATTGGTACATTATTATTCGATCGGTTTTCTGCATCACAGCGAATGG
                  ************************************************************

SAM_Sanger_DNA    YGGATTAAAATTGAGAAATAGAGACCCGCGCCAAATGGCATGTCCACAAAAAATACATTG
SAM_NGS           TGGATTAAAATTGAGAAATAGAGACCCGCGCCAAATGGCATGTCCACAAAAAATACATTG
                   ***********************************************************

SAM_Sanger_DNA    TTTGTAAATAACGGATATATTTGTGTGCATTTTCAGATACGAAACCGAAAACGGCATCGT
SAM_NGS           TTTGTAAATAACGGATATATTTGTGTGCATTTTCAGATACGAAACCGAAAACGGCATCGT
                  ************************************************************

SAM_Sanger_DNA    CGCCCAGGCTGCTGGATACGTTAAGAACGCCGGTTCCGAAAACGCCGTCCAAGTGATCGA
SAM_NGS           CGCCCAGGCTGCTGGATACGTTAAGAACGCCGGTTCCGAAAACGCCGTCCAAGTGATCGA
                  ************************************************************

SAM_Sanger_DNA    AGGCTCGTATGCCTACATCGGTGACGATGGTGCTCCAGTCGAAGTCAAGTACTACGCTGA
SAM_NGS           AGGCTCGTATGCCTACATCGGTGACGATGGTGCTCCAGTCGAAGTCAAGTACTACGCTGA
                  ************************************************************

SAM_Sanger_DNA    CGAGACCGGTTACCACGCAGCCGGAAACGTCGTCCCGACCACTCCCCAGAGATCGCCAA
SAM_NGS           CGAGACCGGTTACCACGCAGCCGGAAACGTCGTCCCGACCACTCCCCAGAGATCGCCAA
                  ************************************************************

SAM_Sanger_DNA    GTCTTTGGAATTAATCGCCTCCCAACCACAGAAACCAGAAGACTCCAAAAAGAA------
SAM_NGS           GTCTTTGGAATTAATCGCCTCCCAACCACAGAAACCAGAAGACTCCAAAAAGAAGTAAAC
                  ******************************************************
```

Figure 2b

```
CATCCCAACATACGGCAATTTTCTGATCACGGTATACGTCCAAAAAAATCACCATGAACACTTTGGTGAGTTAAATAATATTTCTTTAA
ATCTTCTTAAAAAGACATAGCAATATTATCATTTTATTTTTTAATTTAGTTATACAACGCATTGTATAATAGTTTCAATTTATAAACA
GTTTAATTTAAAGAAAAAATAGTATARTTACTGAAATTATTTATTATTTTCGTACTTTATCATACACTTATGAATTTTTAGTATTTTTG
GTATACGAGAATATCTTATTATTTTATAAATATCTTATAAAATAAATGCTCATATTATGTTATACTTATTTTTTAAATTAATGAAACTA
CGAAAAAATTAATTTTAACTCAAATTTTCAAATTTTTTAAGTTCAAATAAGTACCTCAATTTATATTATGAACAGTGTAAAAGTATAAT
ATTTACGTTTACTGCAACCATTATTATATTAGAATCAGTCTTATTATTTTTGTACTTCATAAAAAAATGCCTGAAAATTAAAATTTAAA
AGATATCTCTACAATTTAACGCATAGGTAATCTTATTAATCGTAATCATATTTTAACCAAATCCATATTTTTAGTTTCAATTTAAAATT
GACATTACACCTGTAAAAGTTTTCACAGTATATCTTCACAGCAAAAAATATGCATAAAATTATTTCTTTCCTCAGCACTTTATACAATT
TTCGTGCCTTCGTTTTTAGGTAGTGTTAGTAGCTGTCATCGCAGCGGTGTCTGCTGCGGCCCCACCTCAGGAAGCTGCCAAAGCTTTTA
CTTTCAGTGGATTCCCATCCAACCAAGCCTACTACCCAGGCCAACAAGGGTACTACCCAGGATACATTGGTTACCAGKGTTATCAAGGT
TACAGCGGATTCCGTAATGGATACTACCCGGGACAACAAGGATACTACCCAGGATACAACCAAGGTTACCAGGGATACTACCCAGGATACCA
AGGTTACCAGGGATACTACCCAGGATATCAAGGTTTAATTTCGTTAATTATACGTCTAAAACACTGCAGAGTCACATGATGTGTTATAA
GTTTCTTATAATTTACTATTTTCACATAGGTTACAACCGCGGTTACTACCCAGGTGCCCCAGCCGTCTACCCCACCGTCACCCCCGCCC
CAATCATCGCACCAGTGCCAGTCGCGCCCAAGGCTGTTTCTCCAGTGTACAAACCCGTAGACAACAAAGTGCCAGCTATCCTTAAACAA
TCGCAAGAAGCTGACTTGAACGGATTCAAATACGGGTTAGTATTATAATTGGTACATTATTATTCGATCGGTTTTCTGCATCACAGCGA
ATGGTGGATTAAAATTGAGAAATAGAGACCCGCGCCAAATGGCATGTCCACAAAAAATACATTGTTTGTAAATAACGGATATATTTGTG
TGCATTTTCAGATACGAAACCGAAAACGGCATCGTCGCCCAGGCTGCTGGATACGTTAAGAACGCCGGTTCCGAAAACGCCGTCCAAGT
GATCGAAGGCTCGTATGCCTACATCGGTGACGATGGTGCTCCAGTCGAAGTCAAGTACTACGCTGACGAGACCGGTTACCACGCAGCCG
GAAACGTCGTCCCGACCACTCCCCCAGAGATCGCCAAGTCTTTGGAATTAATCGCCTCCCAACCACAGAAACCAGAAGACTCCAAAAAG
AAGTAAACCCAGCTCGCATGTAACCATCATGTACGCTGAAGATCCCAAACACTCGTATACCATTAGCTATTAGATACCGCATGTGAAA
TCATGCATATTTTTATCATTGCAAATATTGTGTACCTATGCAGTGATTTCGTTATTCGTATCTGAACGACGAATATCGACACATTTAC
TGTACATAGTAATTCAGTTATAATATGTTGGATGTAACAAAAAAAGATGAAAATATAAAAACTTGAAGTTAAATATCGTACAATGTTTT
CTTATTCCACTCGTTAGTCGGTCTTTAAGTCCATGCGTCATGCATCTATGTTATCTTCTAGCAAAAATATATTCTACAAGTTACAAACT
ATGTAGATAACATAATNGNTATTATGTGTTATGTTTAGTAACAGTTCGATTTCGGCACCATCTGCCCGTTTGAATGTGTGATTGTCCGA
AACGTCATGTTACTTGCAAGTAAGTAATAAGCCATAGCTTATTTTTGTGTTTTATCTAATTTGAGGTATATCAGGATACAATGCTAAAA
ACTGCATTGAAATCAAAAAATAAAGAATNAATATCGATGTTAATAATTGTACCTACATACGATTTCTTATTGTTATATTATGTTWATAA
AAAGTCAATGATACACATTTTATAAGATTGTCCATACTTCTTTCATTATAATTTTATGCTCTACACATATCAATCATATTATTTTTAAT
TTTTTTTTGCAAATCAACATACATTTTTTTCCGGGAGTTATCAATTTATCTTTGCCTAATTTAACTAACTMATAAAAATTAATTAGCTG
ATTTATTCGTATGGCATATTTTGACACATAATATACATAAAAAGTTGTAACACGGAATAAAATAAGAATAANANAATAGAATAAAATAA
AATAAAAAATCCATATAAAAAATATTTCTAAATTGTTTAATTGTCTTATTTTAATAATGTGTGGGGAGAATGGTGGTAGCCTGCACG
TGGCCCTCCCTGCATGCGCTTGTAGATTTCCTGAAGACCCTTGTGTACGAAGACAGACTACGAGCGTATCTAATATCACCACCAAAGTG
CTGATACCCAGCAACAGACACAGTAATATGCAGCCTTTAAACGGCCCTTTTCAGGGCGATTCAACGCAGATATTAGGCCCATGCCTTAG
GATATGTCACCTAAATATTGAAGGTATTTCGTCAGCTAAGAGTGAAATTCTATCTAAACTTATGAGAGAGAAAAAAGTTGATGTTATTG
CACTCAAGGAAATTAAATGACGCAATAACAATGTTTATAGTTTTATGCTATTTTACAGTAGTAATTTTGTAGATATTGACACTAAAACA
GAGCGTGCCGCGTAATTATCTGCAAATTAATGTTAGCGAAGCTGGAATAATCATCTCCAAAAAAGAAAAAGATTATCTCTTGAATGAC
TCAATCTAATATTATTGCTGCATTCATATTTCAAATCAAATTTAAAATTCTGAAACGTTGATGGAAAAACTACTGGAAGAAGAAAATTCG
TAAATTGMTACTCAATGAATACTTTTCAGTTAGTACAAAATAATTTATAATTGATAATTAATTTACACTCATAATATACTGTCTCTTAT
ACACATCTAGATGTGTATAAGACACAGGATTGGGATCCAATTTAATAGTGCCTAATAAAAATTATAAAACAAAAATAAATTACTTTTT
ACAATCGATCGTAATAATTGTTTATTTATTTTGTTTACTTAAACTGGCACTTTGACCAAAAATATAAAACCTGTTTGTAAATACATGT
TATTTTGGTACCATCAAATGAAAAAAACTTGCGTGTTTAGTAAATTTATTTCATAGATCACTCTAATATTATTTATGAGTTATGTAAAA
TACATGATGCAATATCAAATGATTTTTTTTTTTATATTAAGCCTCGGCGTCAAAGGCCATTGRTGGAAACAATAAATTAGAGGTAAA
ACATATTTTATTATACATTTAATTTTAGTTGTATTGTTACCAATTTTACCATAAATCATAATAGCCAATTATAAATTATAATGACCACA
TATAAAATGAATTAGGTATTTAAATTTGAATGAGGTTCCAGTTATAACCAAAAAAAAAAAATCACGCAACAGCCGACAAGTAAGTTAT
CGTGTATGAATATTAWWCAAGTAAGTAATTTGTAATTTATATAATTTTATATAAAKAGWTARCGTTTAAATACATAATTGTATAAACGA
GTATTATATAGGAAGGTGTATATTATACGATATTTTACAAACATCTTTTATAGTCGATACAATATAATAGTAGTATTATGATTTTATAA
TTTTAAATTCACTTCCACAGAAGTAAAAACTGCTATATTAAGATTTATCAATAAATAATGATACAGTTCAATTAAATTATGTATATTGT
AATAAGTATTTTGTTTTCATTTTGAAAGGCTTTTAATATATATATATATANTGTATAAATTTTTTTTTTTKTPATTTTTANNAATATAATT
GTATTTATTTATAC
```

Figure 4

A
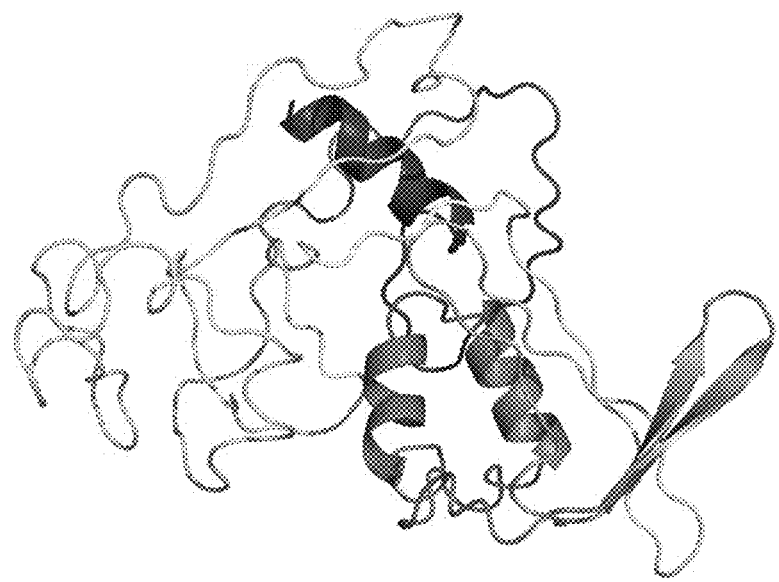
B
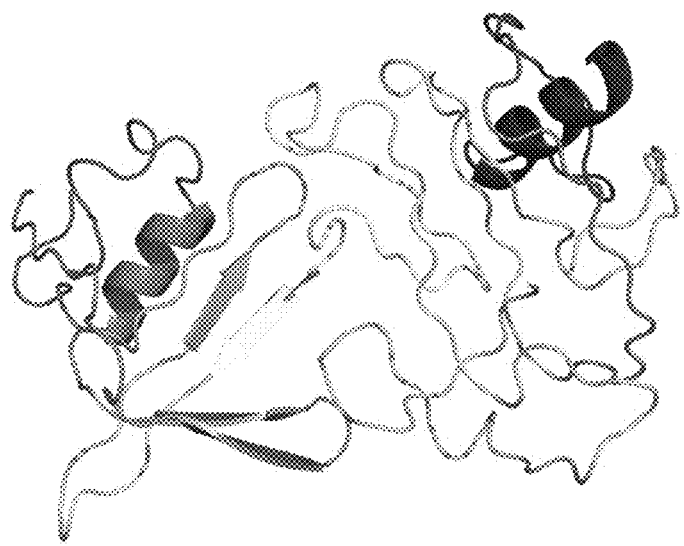
Figure 6

```
SA1_Sanger_cDNA   ---------------------------------------TCCAAAAAAATCACCATGAACA
SAM_NGS           CATCCCAACATACGGCAATTTTCTGATCACGGTATACGTCCAAAAAAATCACCATGAACA
                                                         ***********************

SA1_Sanger_cDNA   CTTTGGTAGTGTTAGTAGCTGTCATCGCAGCGGTGTCTGCTGCGGCCCCACCTCAGGAAG
SAM_NGS           CTTTGGTAGTGTTAGTAGCTGTCATCGCAGCGGTGTCTGCTGCGGCCCCACCTCAGGAAG
                  ************************************************************

SA1_Sanger_cDNA   CTGCCAAAGCTTTTACTTTCAGTGGATTCCCATCCAACCAAGCCTACTACCCAGGCCAAC
SAM_NGS           CTGCCAAAGCTTTTACTTTCAGTGGATTCCCATCCAACCAAGCCTACTACCCAGGCCAAC
                  ************************************************************

SA1_Sanger_cDNA   AAGGGTACTACCCAGGATACATTGGTTACCAGGGTTAYCAAGGTTACAGCGGATTCCGTA
SAM_NGS           AAGGGTACTACCCAGGATACATTGGTTACCAGGGTTATCAAGGTTACAGCGGATTCCGTA
                  ************************************* ********************

SA1_Sanger_cDNA   ATGGATACTACCCGGGACAACAAGGATACTACCCAGGATACCAAGGTTACCAGGGATACT
SAM_NGS           ATGGATACTACCCGGGACAACAAGGATACTACCCAGGATACCAAGGTTACCAGGGATACT
                  ************************************************************

SA1_Sanger_cDNA   ACCCAGGATACCAAGGTTACCAGGGATACTACCCAGGATATCAAGGTTACAACCGCGGTT
SAM_NGS           ACCCAGGATACCAAGGTTACCAGGGATACTACCCAGGATATCAAGGTTACAACCGCGGTT
                  ************************************************************

SA1_Sanger_cDNA   ACTACCCAGGTGCCCCAGCCGTCTACCCCACCGTCACCCCCGCCCCAATCATCGCACCAG
SAM_NGS           ACTACCCAGGTGCCCCAGCCGTCTACCCCACCGTCACCCCCGCCCCAATCATCGCACCAG
                  ************************************************************

SA1_Sanger_cDNA   TGCCAGTCGCGCCCAAGGCTGTTTCTCCAGTGTACAAACCCGTAGACAACAAAGTGCCAG
SAM_NGS           TGCCAGTCGCGCCCAAGGCTGTTTCTCCAGTGTACAAACCCGTAGACAACAAAGTGCCAG
                  ************************************************************

SA1_Sanger_cDNA   CTATCCTTAAACAATCGCAAGAAGCTGACTTGAACGGATTCAAATACGGATACGAAACCG
SAM_NGS           CTATCCTTAAACAATCGCAAGAAGCTGACTTGAACGGATTCAAATACGGATACGAAACCG
                  ************************************************************

SA1_Sanger_cDNA   AAAACGGCATCGTCGCCCAGGCTGCTGGATACGTTAAGAACGCCGGTTCCGAAAACGCCG
SAM_NGS           AAAACGGCATCGTCGCCCAGGCTGCTGGATACGTTAAGAACGCCGGTTCCGAAAACGCCG
                  ************************************************************

SA1_Sanger_cDNA   TCCAAGTGATCGAAGGCTCGTATGCCTACATCGGTGACGATGGTGCTCCAGTCGAAGTCA
SAM_NGS           TCCAAGTGATCGAAGGCTCGTATGCCTACATCGGTGACGATGGTGCTCCAGTCGAAGTCA
                  ************************************************************

SA1_Sanger_cDNA   AGTACTACGCTGACGAGACCGGTTACCACGCAGCCGGAAACGTCGTCCCGACCACTCCCC
SAM_NGS           AGTACTACGCTGACGAGACCGGTTACCACGCAGCCGGAAACGTCGTCCCGACCACTCCCC
                  ************************************************************

SA1_Sanger_cDNA   CAGAGATCGCCAAGTCTTTGGAATTAATCGCCTCCC------------------------
SAM_NGS           CAGAGATCGCCAAGTCTTTGGAATTAATCGCCTCCCAACCACAGAAACCAGAAGACTCCA
                  ***********************************

SA1_Sanger_cDNA   ------------------------------------------------
SAM_NGS           AAAAGAAATCACTCTAATATTATTTATGAGTTATGTAAAATACATG
```

Figure 7

```
SAM_Sanger_cDNA   ------------------------------------------TCCAAAAAAATCACCATGAACA
SAM_NGS           CATCCCAACATACGGCAATTTTCTGATCACGGTATACGTCCAAAAAAATCACCATGAACA
                                                            ********************

SAM_Sanger_cDNA   CTTTGGTAGTGTTAGTAGCTGTCATCGCAGCGGTGTCTGCTGCGGCCCCACCTCAGGAAG
SAM_NGS           CTTTGGTAGTGTTAGTAGCTGTCATCGCAGCGGTGTCTGCTGCGGCCCCACCTCAGGAAG
                  ************************************************************

SAM_Sanger_cDNA   CTGCCAAAGCTTTTACTTTCAGTGGATTCCCATCCAACCAAGCCTACTACCCAGGCCAAC
SAM_NGS           CTGCCAAAGCTTTTACTTTCAGTGGATTCCCATCCAACCAAGCCTACTACCCAGGCCAAC
                  ************************************************************

SAM_Sanger_cDNA   AAGGGTACTACCCAGGATACATTGGTTACCAGGGTTAYCAAGGTTACAGCGGATTCCGTA
SAM_NGS           AAGGGTACTACCCAGGATACATTGGTTACCAGGGTTATCAAGGTTACAGCGGATTCCGTA
                  ************************************** *********************

SAM_Sanger_cDNA   ATGGATACTACCCGGGACAACAAGGATACTACCCAGGATACCAAGGTTACCAGGGATACT
SAM_NGS           ATGGATACTACCCGGGACAACAAGGATACTACCCAGGATACCAAGGTTACCAGGGATACT
                  ************************************************************

SAM_Sanger_cDNA   ACCCAGGATACCAAGGTTACCAGGGATACTACCCAGGATATCAAGGTTACAACCGCGGTT
SAM_NGS           ACCCAGGATACCAAGGTTACCAGGGATACTACCCAGGATATCAAGGTTACAACCGCGGTT
                  ************************************************************

SAM_Sanger_cDNA   ACTACCCAGGTGCCCCAGCCGTCTACCCCACCGTCACCCCGCCCCAATCATCGCACCAG
SAM_NGS           ACTACCCAGGTGCCCCAGCCGTCTACCCCACCGTCACCCCGCCCCAATCATCGCACCAG
                  ***********************************************************

SAM_Sanger_cDNA   TGCCAGTCGCGCCCAAGGCTGTTTCTCCAGTGTACAAACCCGTAGACAACAAAGTGCCAG
SAM_NGS           TGCCAGTCGCGCCCAAGGCTGTTTCTCCAGTGTACAAACCCGTAGACAACAAAGTGCCAG
                  ************************************************************

SAM_Sanger_cDNA   CTATCCTTAAACAATCGCAAGAAGCTGACTTGAACGGATTCAAATACGGATACGAAACCG
SAM_NGS           CTATCCTTAAACAATCGCAAGAAGCTGACTTGAACGGATTCAAATACGGATACGAAACCG
                  ************************************************************

SAM_Sanger_cDNA   AAAACGGCATCGTCGCCCAGGCTGCTGGATACGTTAAGAACGCCGGTTCCGAAAACGCCG
SAM_NGS           AAAACGGCATCGTCGCCCAGGCTGCTGGATACGTTAAGAACGCCGGTTCCGAAAACGCCG
                  ************************************************************

SAM_Sanger_cDNA   TCCAAGTGATCGAAGGCTCGTATGCCTACATCGGTGACGATGGTGCTCCAGTCGAAGTCA
SAM_NGS           TCCAAGTGATCGAAGGCTCGTATGCCTACATCGGTGACGATGGTGCTCCAGTCGAAGTCA
                  ************************************************************

SAM_Sanger_cDNA   AGTACTACGCTGACGAGACCGGTTACCACGCAGCCGGAAACGTCGTCCCGACCACTCCCC
SAM_NGS           AGTACTACGCTGACGAGACCGGTTACCACGCAGCCGGAAACGTCGTCCCGACCACTCCCC
                  ************************************************************

SAM_Sanger_cDNA   CAGAGATCGCCAAGTCTTTGGAATTAATCGCCTCCCAACCACAGAAAC------------
SAM_NGS           CAGAGATCGCCAAGTCTTTGGAATTAATCGCCTCCCAACCACAGAAACCAGAAGACTCCA
                  ***********************************************

SAM_Sanger_cDNA   ------------------------------------------------
SAM_NGS           AAAAGAAATCACTCTAATATTATTTATGAGTTATGTAAAATACATG
```

Figure 8

CAUCCCAACAUACGGCAAUUUUCUGAUCACGGUAUACGUCCAAAAAAAUCACCAUGAACACUUUGGUAGUGUUAGUAGCU
GUCAUCGCAGCGGUGUCUGCUGCGGCCCCACCUCAGGAAGCUGCCAAAGCUUUUACUUUCAGUGGAUUCCCAUCCAACCA
AGCCUACUACCCAGGCCAACAAGGGUACUACCCAGGAUACAUUGGUUACCAGGGUUAYCAAGGUUACAGCGGAUUCCGUA
AUGGAUACUACCCGGGACAACAAGGAUACUACCCAGGAUACCAAGGUUACCAGGGAUACUACCCAGGAUACCAAGGUUAC
CAGGGAUACUACCCAGGAUAUCAAGGUUACAACCGCGGUUACUACCCAGGUGCCCCAGCCGUCUACCCCACCGUCACCCC
CGCCCCAAUCAUCGCACCAGUGCCAGUCGCGCCCAAGGCUGUUUCUCCAGUGUACAAACCCGUAGACAACAAAGUGCCAG
CUAUCCUUAAACAAUCGCAAGAAGCUGACUUGAACGGAUUCAAAUACGGAUACGAAACCGAAAACGGCAUCGUCGCCCAG
GCUGCUGGAUACGUUAAGAACGCCGGUUCCGAAAACGCCGUCCAAGUGAUCGAAGGCUCGUAUGCCUACAUCGGUGACGA
UGGUGCUCCAGUCGAAGUCAAGUACUACGCUGACGAGACCGGUUACCACGCAGCCGGAAACGUCGUCCCGACCACUCCCC
CAGAGAUCGCCAAGUCUUUGGAAUUAAUCGCCUCCCAACCACAGAAACCAGAAGACUCCAAAAAGAAAUCACUCUAAUAU
UAUUUAUGAGUUAUGUAAAAUACAUGAUGCAAUAUCAAAUGAUUUUUUUUUUUUUUAUAUUAAGCCUCGGCGUCAAAGGCC
AUUGRUGGAAACAAUAAAUUAGAGGGUAAAACAUAUUUUAUUAUACAUUUAAUUUUAGUUGUAUUGUUACCAAUUUUUACCA
UAAAUCAUAAUAGCCAAUUAUAAAUUAUAAUGACCACAUAUAAAAUGAAUUAGGUAUUUAAAAUUUGAAUGAGGUUCCAGU
UAUAACCAAAAAAAAAAAAAAUCACGCAACAGCCGACAAGUAAGUUAUCGUGUAUGAACAUUAWWCAAGUAAGUAAUUUGU
AAUUUAUAUAAUUUUAUAUAAAKAGWUARCGUUUAAAUACAUAAUUGUAUAAACGAGUAUUAUAUAGGAAGGUGUAUAUU
AUACGAUAUUUUACAAACAUCUUUUAUAGUCGAUACAAUAUAAUAGUAGUAUUAUGAUUUUAUAAUUUUAAAUUCACUUC
CACAGAAGUAAAAACUGCUAUAUUAAGAUUUAUCAAUAAAUAAUGAUACAGUUCAAUUAAAUUAUGUAUAUUGUAAUAAG
UAUUUUGUUUUCAUUUUGAAAGGCUUUUAAUAUAUAUAUAUANUGUAUAAAUUUUUUUUUUUUKURAUUUUUANNAAUAUA
AUUUGUAUUUAUUUAUAC

Figure 9

ATGAACACTTTGGTAGTGTTAGTAGCTGTCATCGCAGCGGTGTCTGCTGCGGCCCCACCTCAGGAAGCTGCC
AAAGCTTTTACTTTCAGTGGATTCCCATCCAACCAAGCCTACTACCCAGGCCAACAAGGGTACTACCCAGGA
TACATTGGTTACCAGGGTTATCAAGGTTACAGCGGATTCCGTAATGGATACTACCCGGGACAACAAGGATAC
TACCCAGGATACCAAGGTTACCAGGGATACTACCCAGGATACCAAGGTTACCAGGGATACTACCCAGGATAT
CAAGGTTACAACCGCGGTTACTACCCAGGTGCCCCAGCCGTCTACCCCACCGTCACCCCCGCCCCAATCATC
GCACCAGTGCCAGTCGCGCCCAAGGCTGTTTCTCCAGTGTACAAACCCGTAGACAACAAAGTGCCAGCTATC
CTTAAACAATCGCAAGAAGCTGACTTGAACGGATTCAAATACGGATACGAAACCGAAAACGGCATCGTCGCC
CAGGCTGCTGGATACGTTAAGAACGCCGGTTCCGAAAACGCCGTCCAAGTGATCGAAGGCTCGTATGCCTAC
ATCGGTGACGATGGTGCTCCAGTCGAAGTCAAGTACTACGCTGACGAGACCGGTTACCACGCAGCCGGAAAC
GTCGTCCCGACCACTCCCCCAGAGATCGCCAAGTCTTTGGAATTAATCGCCTCCCAACCACAGAAACCAGAA
GACTCCAAAAAGAAATCACTCTAA

Figure 10

```
CGGTATACGTCCAAAAAAATCACCATGAACACTTTGGTGAGTTAAATAATATTTCTTTAAATCTTCTTAAAAAAGACATA
GCAATATTATCATTTTATTTTTTAATTTAGTTATACAACGCATTGTATAATAGTTTCAATTTATAAACAGTTTAATTTAA
AGAAAAAATAGTATARTTACTGAAATTATTTATTATTTTCGTACTTTATCATACACTTATGAATTTTTAGTATTTTTGGT
ATACGAGAATATCTTATTATTTTATAAATATCTTATAAAATAAATGCTCATATTATGTTATACTTATTTTTTAAATTAAT
GAAACTACGAAAAAATTAATTTTAACTCAAATTTTCAAATTTTTTAAGTTCAAATAAGTACCTCAATTTATATTATGAAC
AGTGTAAAAGTATAATATTTACGTTTACTGCAACCATTATTATATTAGAATCAGTCTTATTATTTTTGTACTTCATAAAA
AAATGCCTGAAAATTAAAATTTAAAAGATATCTCTACAATTTAACGCATAGGTAATCTTATTAATCGTAATCATATTTTA
ACCAAATCCATATTTTTAGTTTCAATTTAAAATTGACATTACACCTGTAAAAGTTTTCACAGTATATCTTCACAGCAAAA
AATATGCATAAAATTATTTCTTTCCTCAGCACTTTATACAATTTTCGTGCCTTCGTTTTAGGTAGTGTTAGTAGCTGTC
ATCGCAGCGGTGTCTGCTGCGGCCCCACCTCAGGAAGCTGCCAAAGCTTTTACTTTCAGTGGATTCCCATCCAACCAAGC
CTACTACCCAGGCCAACAAGGGTACTACCCAGGATACATTGGTTACCAGKGTTATCAAGGTTACAGCGGATTCCGTAATG
GATACTACCCGGGACAACAAGGATACTACCCAGGATACCAAGGTTACCAGGGATACTACCCAGGATACCAAGGTTACCAG
GGATACTACCCAGGATATCAAGGTTTAATTTCGTTAATTATACGTCTAAAACACTGCAGAGTCACATGATGTGTTATAAG
TTTCTTATAATTTACTATTTTCACATAGGTTACAACCGCGGTTACTACCCAGGTGCCCCAGCCGTCTACCCCACCGTCAC
CCCCGCCCCAATCATCGCACCAGTGCCAGTCGCGCCCAAGGCTGTTTCTCCAGTGTACAAACCCGTAGACAACAAAGTGC
CAGCTATCCTTAAACAATCGCAAGAAGCTGACTTGAACGGATTCAAATACGGGTTAGTATTATAATTGGTACATTATTAT
TCGATCGGTTTTCTGCATCACAGCGAATGGYGGATTAAAATTGAGAAATAGAGACCCGCGCCAAATGGCATGTCCACAAA
AAATACATTGTTTGTAAATAACGGATATATTTGTGTGCATTTTCAGATACGAAACCGAAAACGGCATCGTCGCCCAGGCT
GCTGGATACGTTAAGAACGCCGGTTCCGAAAACGCCGTCCAAGTGATCGAAGGCTCGTATGCCTACATCGGTGACGATGG
TGCTCCAGTCGAAGTCAAGTACTACGCTGACGAGACCGGTTACCACGCAGCCGGAAACGTCGTCCCGACCACTCCCCCAG
AGATCGCCAAGTCTTTGGAATTAATCGCCTCCCAACCACAGAAACCAGAAGACTCCAAAAGAA
```

Figure 11

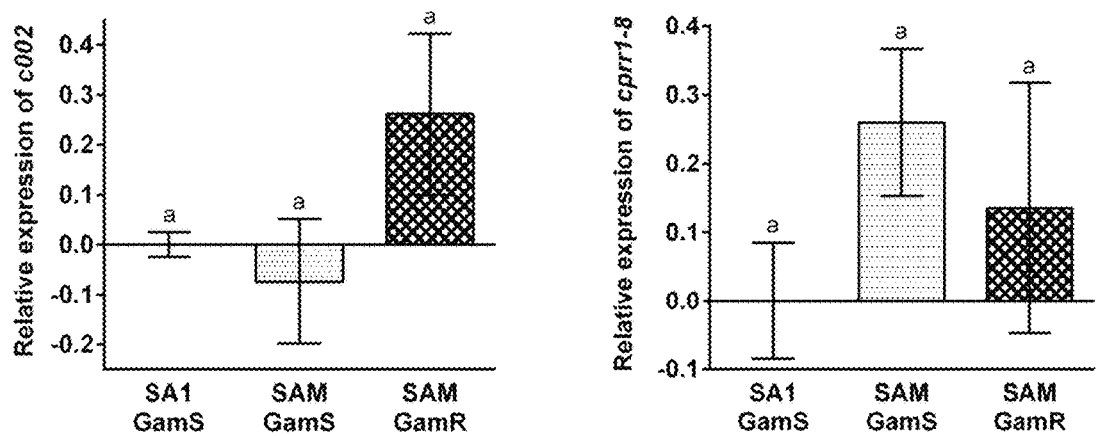

Figure 12

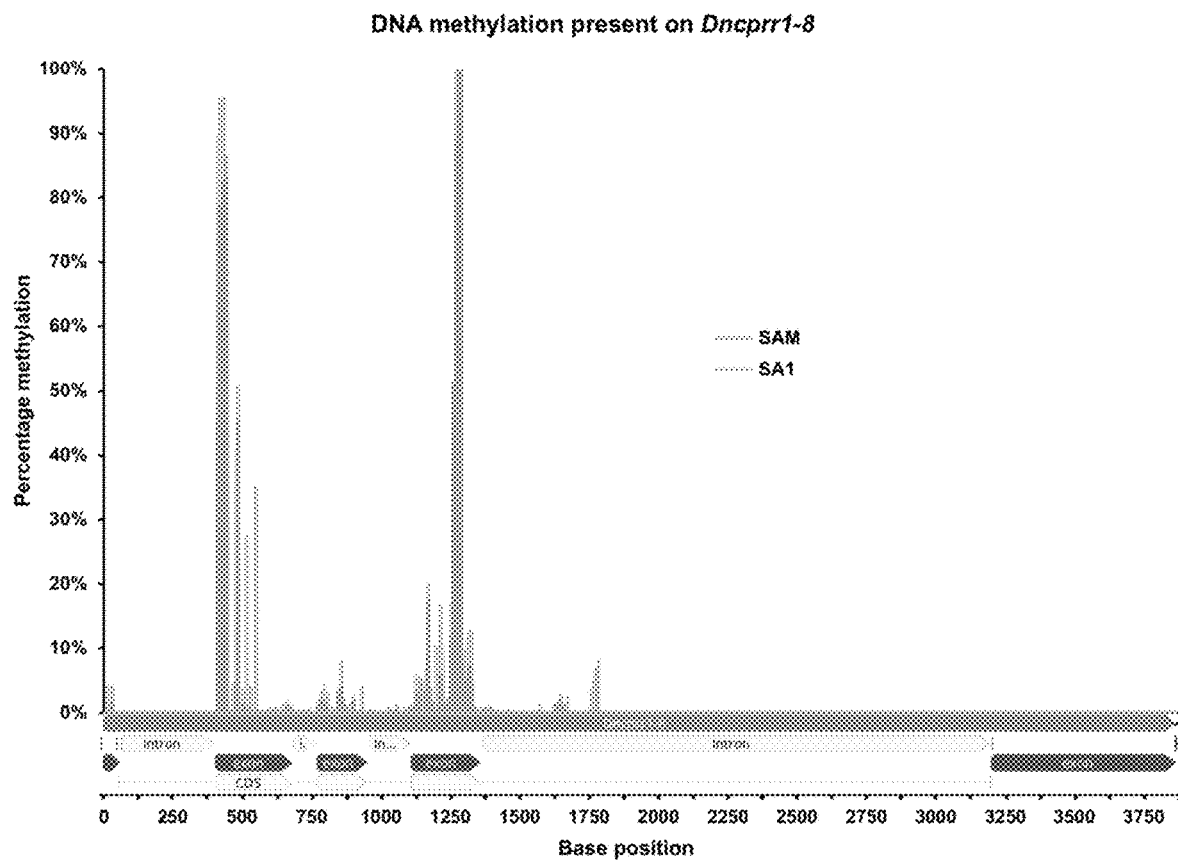

Figure 18

```
CAAAGTGCCAGCTATCCTTAAACAATCGCAAGAAGCTGACTTGAACGGATTCAAATACGGATACGAAACCGAAAACGGCA
TCGTCGCCCAGGCTGCTGGATACGTTAAGAACGCCGGTTCCGAAAACGCCGTCCAAGTGATCGAAGGCTCGTATGCCTAC
ATCGGTGACGATGGTGCTCCAGTCGAAGTCAAGTACTACGCTGACGAGACCGGTTACCACGCAGCCGGAAACGTCGTCCC
GACCACTCCCCCAGAGATCGCCAAGTCTTTGGAATTAATCGCCTCCCAACCACAGAAACCA
```

Figure 19

METHOD FOR CONTROLLING PEST INFESTATIONS

CROSS-REFERENCE TO RELATED APPLICATIONS

This application claims priority from South African provisional patent application number 2018/01488 filed on 5 Mar. 2018.

FIELD OF THE INVENTION

The present invention relates to methods for controlling pest infestation using a siRNA molecule. The invention provides methods for making transgenic plants that express the siRNA molecule, as well as pesticidal agents and commodity products produced by the plants.

BACKGROUND TO THE INVENTION

Insect pests are one of the largest causes of crop losses in the agricultural sector. The emergence of host plant resistance is a natural way in which crop losses due to insect pests are sometimes limited, but unfortunately this is often counteracted by the rapid emergence of new insect biotypes that are virulent to the now previously resistant cultivar.

The Russian wheat aphid (RWA) (*Diuraphis noxia*, Kurdjomov) is one such example. This aphid has a narrow host range, consisting mainly of wheat, barley and other grasses and is found in all the major wheat producing countries. Of the 14 resistance genes in wheat, only Dn7 and Dn2401 remain effective to existing *D. noxia* biotypes in the USA. The same is true in South Africa, where only Dn7 confers effective resistance against the four biotypes present (Dn2401 is yet to be screened against South African biotypes).

Chemical insecticides can also be used to control some insect pests, but this is not always desirable, as the insecticides may be harmful to the environment.

There is therefore a need to develop agricultural crops which have durable resistance to insect pests.

SUMMARY OF THE INVENTION

According to a first embodiment of the invention, there is provided an siRNA molecule targeting the mature mRNA of *D. noxia* cprr1-8 in a region between nucleotides 464 and 774 of SEQ ID NO: 23, or an equivalent region of an ortholog of *D. noxia* cprr1-8.

The region targeted by the siRNA molecule may be a contiguous sequence of from 19 to 25 nucleotides.

The siRNA molecule may target the mature mRNA of *D. noxia* cprr1-8 in a region between nucleotides 485 and 720 of SEQ ID NO: 23, such as nucleotides 486-508, between about nucleotides 509 and 720 or between about nucleotides 464 and 774.

The siRNA molecule may comprise a polynucleotide which has at least 80%, 85%, 90%, 95% or 100% sequence identity to the sequence 5' UAAACAAUCGCAAGAAGCUGA 3' (SEQ ID NO: 1) and a polynucleotide which has at least 80%, 85%, 90%, 95% or 100% sequence identity to the sequence 5' AGCUUCUUGCGAUUGUUUAAG 3' (SEQ ID NO: 2).

The siRNA molecule may consist of the duplex:

```
                                        (SEQ ID NO: 1)
        5' UAAACAAUCGCAAGAAGCUGA 3'

(SEQ ID NO: 2)
        5' AGCUUCUUGCGAUUGUUUAAG 3'.
```

The siRNA molecule may comprise a deoxyribonucleotide and/or a modification.

According to a second embodiment of the invention, there is provided a composition comprising an siRNA molecule as described above and a carrier and/or excipient.

According to a third embodiment of the invention, there is provided an isolated polynucleotide or set of polynucleotides encoding an siRNA molecule as described above.

The isolated polynucleotide may have a sequence which is at least 80% identical to SEQ ID NO: 3.

According to a fourth embodiment of the invention, there is provided a vector encoding the siRNA molecule as described above.

The vector may comprise a polynucleotide having a sequence which is at least 80% identical to SEQ ID NO: 3.

According to a fifth embodiment of the invention, there is provided a plant or plant part which has been transformed to express an siRNA molecule as described above.

According to a further embodiment of the invention, there is provided the use of an siRNA molecule or a composition as described above for inhibiting the biological activity of a pest.

According to a further embodiment of the invention, there is provided a method for controlling pest infestation, the method comprising providing a pest with an siRNA molecule as described above.

According to a further embodiment of the invention, there is provided a method for controlling pest infestation, the method comprising:
  (a) introducing an siRNA molecule as described above into a plant or transforming the plant with a polynucleotide which causes the plant to express the siRNA molecule; and
  (b) providing the plant, or portion thereof, to the pest.

According to a further embodiment of the invention, there is provided a method for improving crop yield, the method comprising:
  a) transforming the plant with a polynucleotide which causes the plant to express an siRNA molecule as described above; and
  b) cultivating the plant to allow expression of the siRNA molecules, wherein the expression inhibits feeding by a pest and loss of yield due to pest infestation.

The plant may be selected from the group consisting of wheat, barley, sugarcane, maize, rice, rye, sorghum, soya, palm, potato, cassava, sugar beet, banana, citrus, grapes, apple, watermelon, mango, cucumber, tomato, brassica species like rapeseed, tea, coffee, tobacco, cannabis, cotton and ornamental plants such as roses. More particularly, the plant is wheat.

The pest may be an insect, including aphids (e.g. *Diuraphis noxia, Myzus persicae, Aphis fabae, Aphis glycines, Brevicoryne brassicae, Aphis gossypii, Macrosiphum euphorbiae, Acyrthosiphon pisum, Dysaphis plantaginea, Aphis craccivora, Schizaphis graminum, Rhopalosiphum padi, Rhopalosiphum maidis, Sitobion avenae*), whitefly, Thrips, Lepidoptera larva, Diptera larva, Coleoptera larva, Tetranychidae, Gryllidae or Caelifera. More particularly, the insect is *Diuraphis noxia*.

BRIEF DESCRIPTION OF THE FIGURES

FIGS. 1a and b SA1 Dncprr1-8 (DNA) alignment. Sanger sequence of SA1 Dncprr1-8 (DNA) (SEQ ID NO: 4) aligned to Dncprr1-8 obtained from the SAM genome sequence (SEQ ID NO: 5). Alignment performed using MUSCLE (3.8) (Edgar 2004).

FIGS. 2a and b SAM Dncprr1-8 (DNA) alignment. Sanger sequence of SAM Dncprr1-8 (DNA) (SEQ ID NO: 6) aligned to Dncprr1-8 obtained from the SAM genome sequence (SEQ ID NO: 5). Alignment performed using MUSCLE (3.8) (Edgar 2004).

FIG. 4 Sequence of *D. noxia* larval cuticle protein gene, cprr1-8 (SEQ ID NO: 7). Regular font—exons, italics—introns, bold—start and stop codons, underlining—coding domain sequence, double underlining—primer binding sites, last nucleotide—transcription end site. Primer biding sites are:

```
                                      (SEQ ID NO: 8)
qPCR F-CCCATCCAACCAAGCCTA (SEQ ID NO: 9)
qPCR R-CCGGGACAACAAGGATACTA (SEQ ID NO: 10)
(Primer 5'-3': TAGTATCCTTGTTGTCCCGG);

(SEQ ID NO: 11)
RNAi-L F-GTAGACAACAAAGTGCCAGC (SEQ ID NO: 12)
RNAi-L R-AATTAATCGCCTCCCAACCA (SEQ ID NO: 13)
(Primer 5'-3': TGGTTGGGAGGCGATTAATT)

(SEQ ID NO: 14)
RNAi-S F-AAAACGCCGTCCAAGTGATC (SEQ ID NO: 15)
RNAi-S R-GGTGCTCCAGTCGAAGTCAA (SEQ ID NO: 16)
(Primer 5'-3': TTGACTTCGACTGGAGCACC).
```

Figure 5:
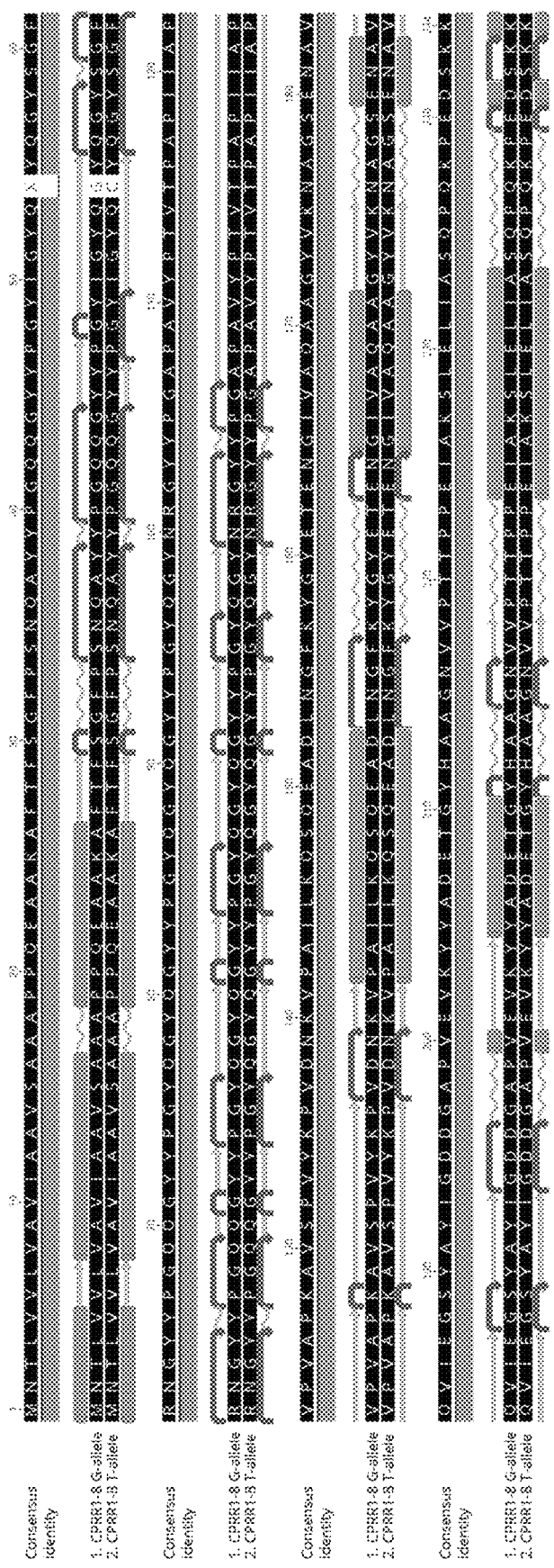

FIG. 5 Protein alignment and secondary structure of the CPRR1-8 G- and T-alleles (Consensus sequence=SEQ ID NO: 17). The T-allele was found in SAM clone #2 (SEQ ID NO: 18), while the other SA1 and SAM clones result in the same amino acid sequence as the G-allele (SEQ ID NO: 19). The length of beta-strands was different and an additional coil was observed on the original G-allele when the secondary structure of the two alleles were compared. The secondary structure was annotated using the EMBOSS 6.5.7 tool gamier.

Graphic was generated in Geneious 9.1.8 (Biomatters). ▓, alfa helix; ➡, beta strand; ⋂, turn; ᴗ coil.

FIG. 6 Predicted tertiary structure of the G-(A) and T-allele (B) of CPRR1-8. Predicted models were obtained with Phyre2 web portal.

FIG. 7 SA1 Dncprr1-8 transcript (cDNA) alignment. Sanger sequence of the biotype SA1 Dncprr1-8 transcript (cDNA) (SEQ ID NO: 20) aligned to the in silico predicted SAM Dncprr1-8 (SEQ ID NO: 21) transcript from the SAM genome sequence. Alignment performed using MUSCLE (3.8) (Edgar 2004).

FIG. 8 SAM Dncprr1-8 transcript (cDNA) alignment. Sanger sequence of SAM Dncprr1-8 transcript (cDNA) (SEQ ID NO: 22) aligned to the in silico predicted SAM Dncprr1-8 transcript from the SAM genome sequence (SEQ ID NO: 21). Alignment performed using MUSCLE (3.8) (Edgar 2004).

FIG. 9 Mature mRNA of *D. noxia* larval cuticle protein cprr1-8> (SEQ ID NO: 23). Bold, primer binding sites; underlining, start and stop codons; double underlining, sequence to be translated into the Rebers and Riddiford chitin binding domain; dashed underlining, siRNA binding area; italics, conserved cuticle protein sequence.

FIG. 10 CDS *Diuraphis noxia* larval cuticle protein cprr1-8> (SEQ ID NO: 24). Primer binding sites are underlined.

FIG. 11 NGS sequence: *D. noxia* larval cuticle protein gene, cprr1-8> (SEQ ID NO: 25).

FIG. 12 Relative qPCR expression of Dnc002 (A) and Dncprr1-8 (B) in *D. noxia* biotype SA1 and SAM after feeding on susceptible wheat cultivar 'Gamtoos-S' (GamS) or resistant 'Gamtoos-R' (GamR) for at least 10 days.

Figure 13:
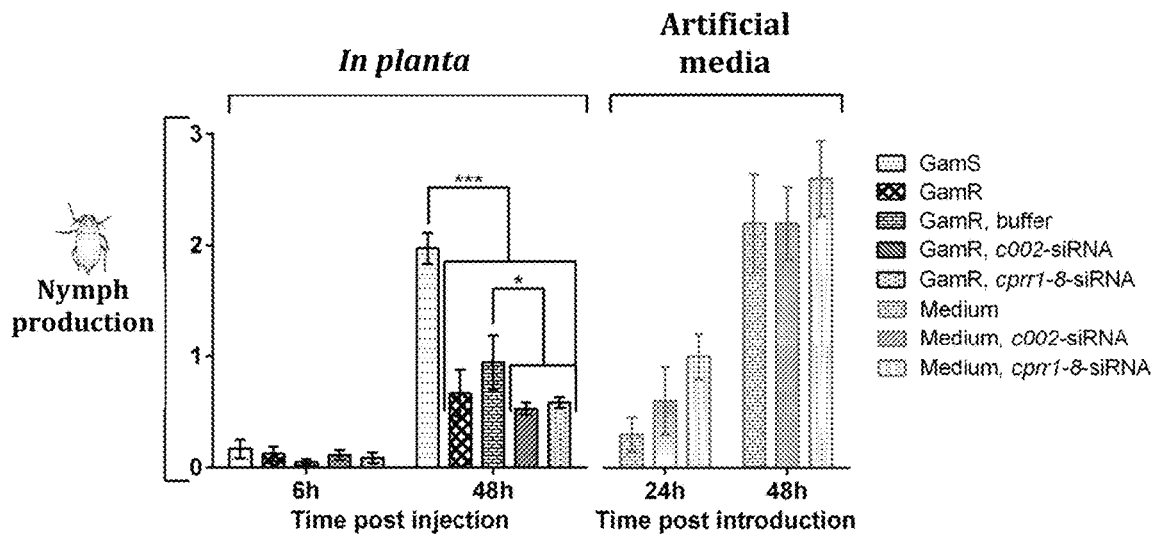

FIG. 13 Nymph production of *D. noxia* biotype SAM after feeding on wheat leaves injected with siRNA (19 nt duplex region and a 2 nt 3'-overhang) that targets the genes c002 or cprr1-8. siRNA was dissolved in 10 mM Tris (pH 7.0) before injection. GamS, susceptible wheat cultivar 'Gamtoos-S'; GamR, resistant wheat cultivar 'Gamtoos-R'; No injection, wheat leaves without injection; Buffer, 10 mM Tris (pH 7); c002-siRNA, siRNA targeting c002 dissolved in 10 mM Tris (pH 7); cprr1-8-siRNA, siRNA targeting cprr1-8 dissolved in 10 mM Tris (pH 7).

Figure 14:
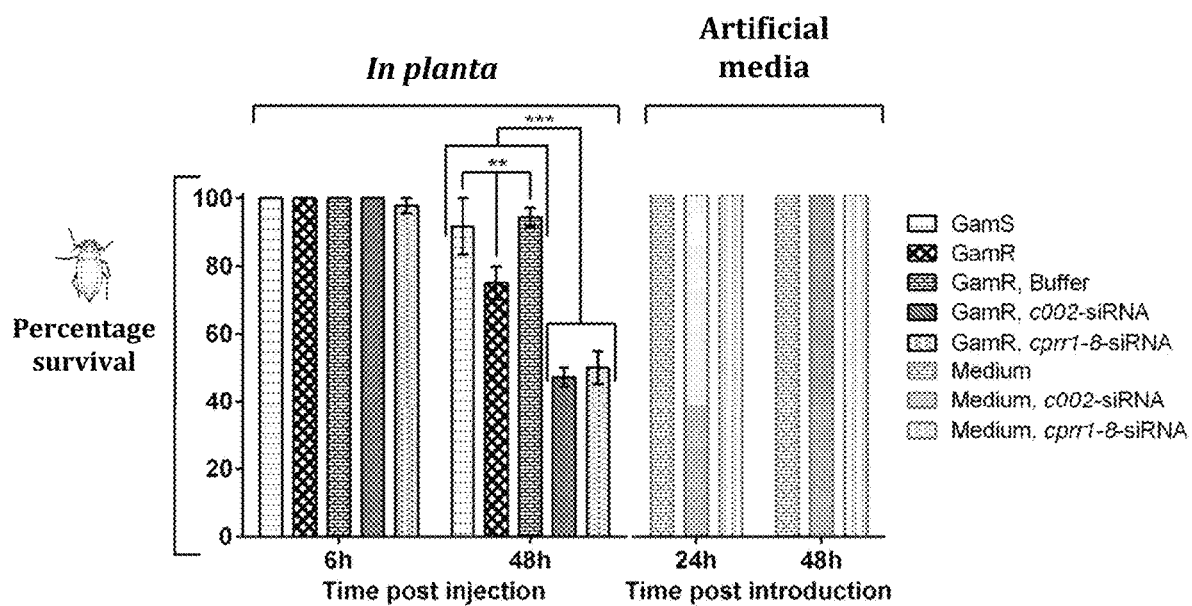

FIG. 14 Percentage survival of *D. noxia* biotype SAM after feeding on wheat leaves injected with siRNA that targets the *D. noxia* genes c002 or cprr1-8. GamS, *D. noxia* susceptible wheat cultivar 'Gamtoos-S'; GamR, *D. noxia* resistant wheat cultivar 'Gamtoos-R'; Buffer, 10 mM Tris (pH 7); c002-siRNA, siRNA targeting c002 dissolved in 10 mM Tris (pH 7); cprr1-8-siRNA, siRNA targeting cprr1-8 dissolved in 10 mM Tris (pH 7); , significantly different at P 0.01; *, significantly different at P 0.001. Error bars represent SEM.

Figure 15:
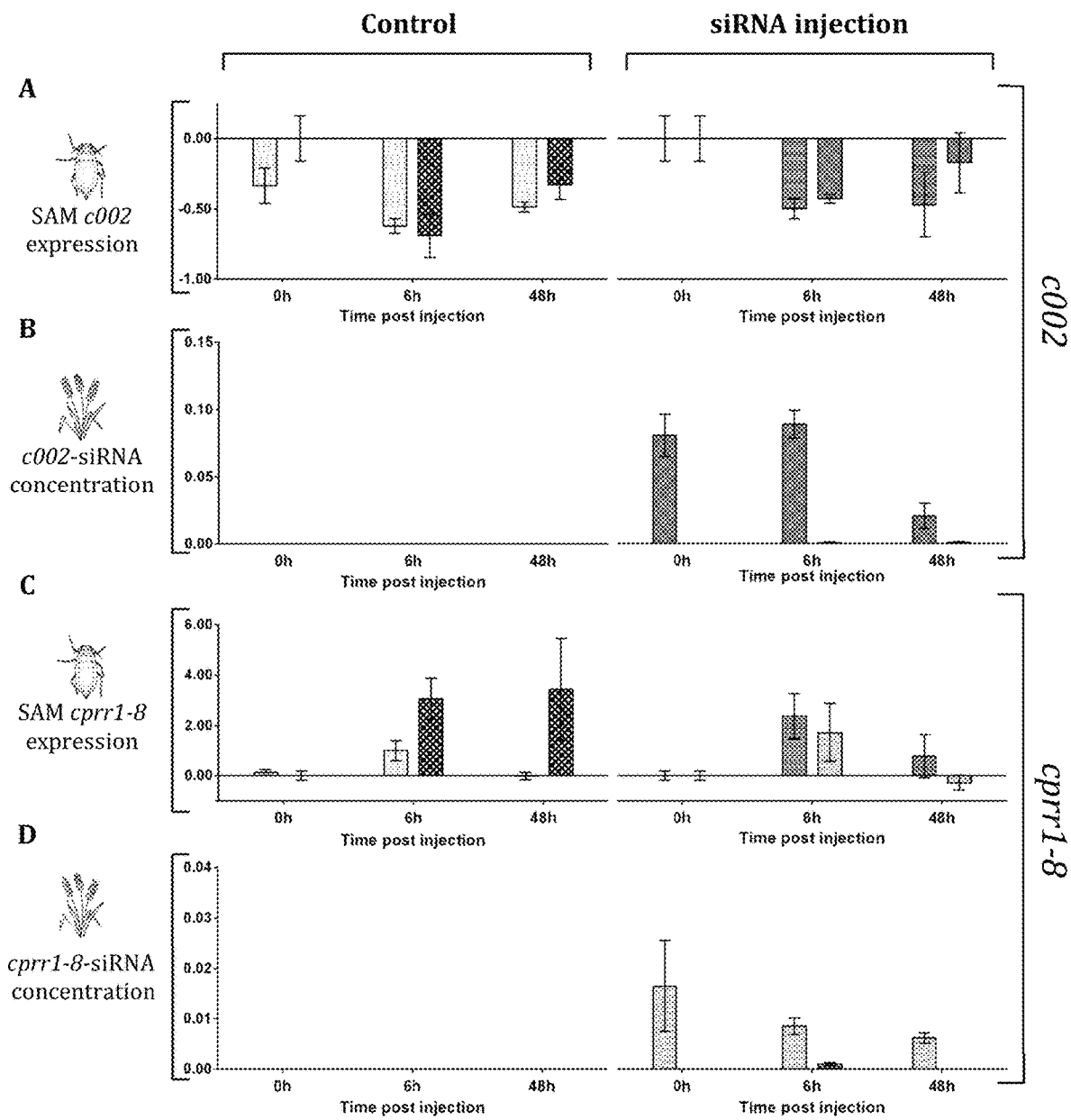

FIG. 15 *D. noxia* biotype SAM was allowed to feed on wheat cultivar Gamtoos-R injected with Dnc002-siRNA, Dncprr1-8-siRNA or buffer (control, no siRNA). *D. noxia* biotype SAM was also allowed to feed on wheat cultivar Gamtoos-R and Gamtoos-S that was not injected (control). Relative expression of *D. noxia* biotype SAM c002 (A) cprr1 (B) was determined with qPCR while SAM fed on wheat injected with siRNA. ▢, Gamtoos-S, No injection; ▨, Gamtoos-R, No injection; ▩, Gamtoos-R, Buffer injection; ▨, Gamtoos-R, c002-siRNA injection; ▨, Gamtoos-R, cprr1-8-siRNA injection. qPCR was also used to determine the c002-siRNA (C) or cprr1-8-siRNA (D) concentration in the injected wheat leaf on which *D. noxia* biotype SAM fed. Error bars represent SEM.

Figure 16:
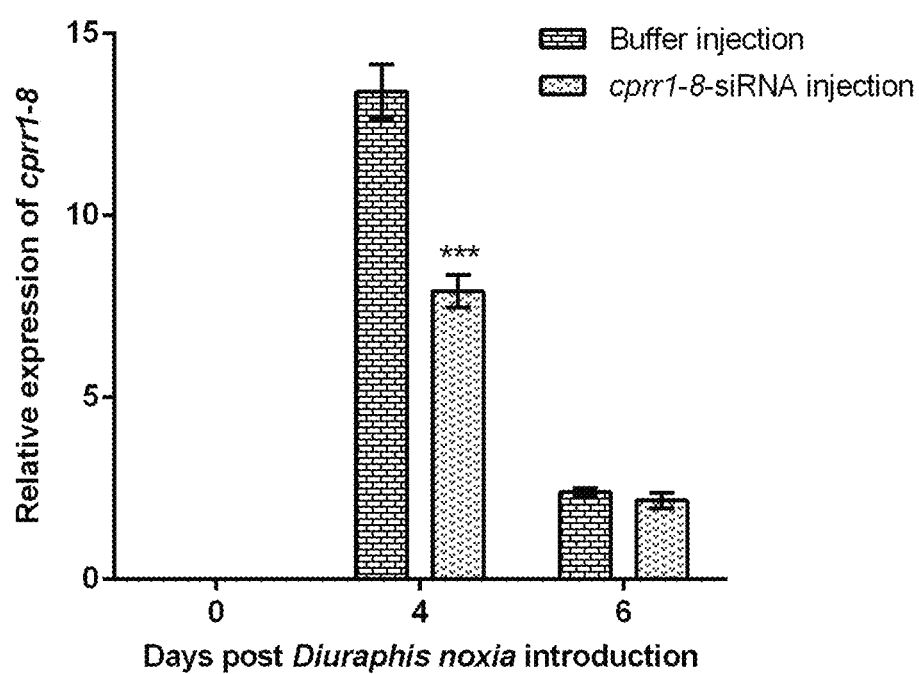

FIG. 16 Relative cprr1-8 expression after feeding on cprr1-8-siRNA injected wheat. Nymphs of *D. noxia* feeding on 'Gamtoos R' injected with cprr1-8 were used for gene expression analysis of cprr1-8 via RT-qPCR.

Figure 17:
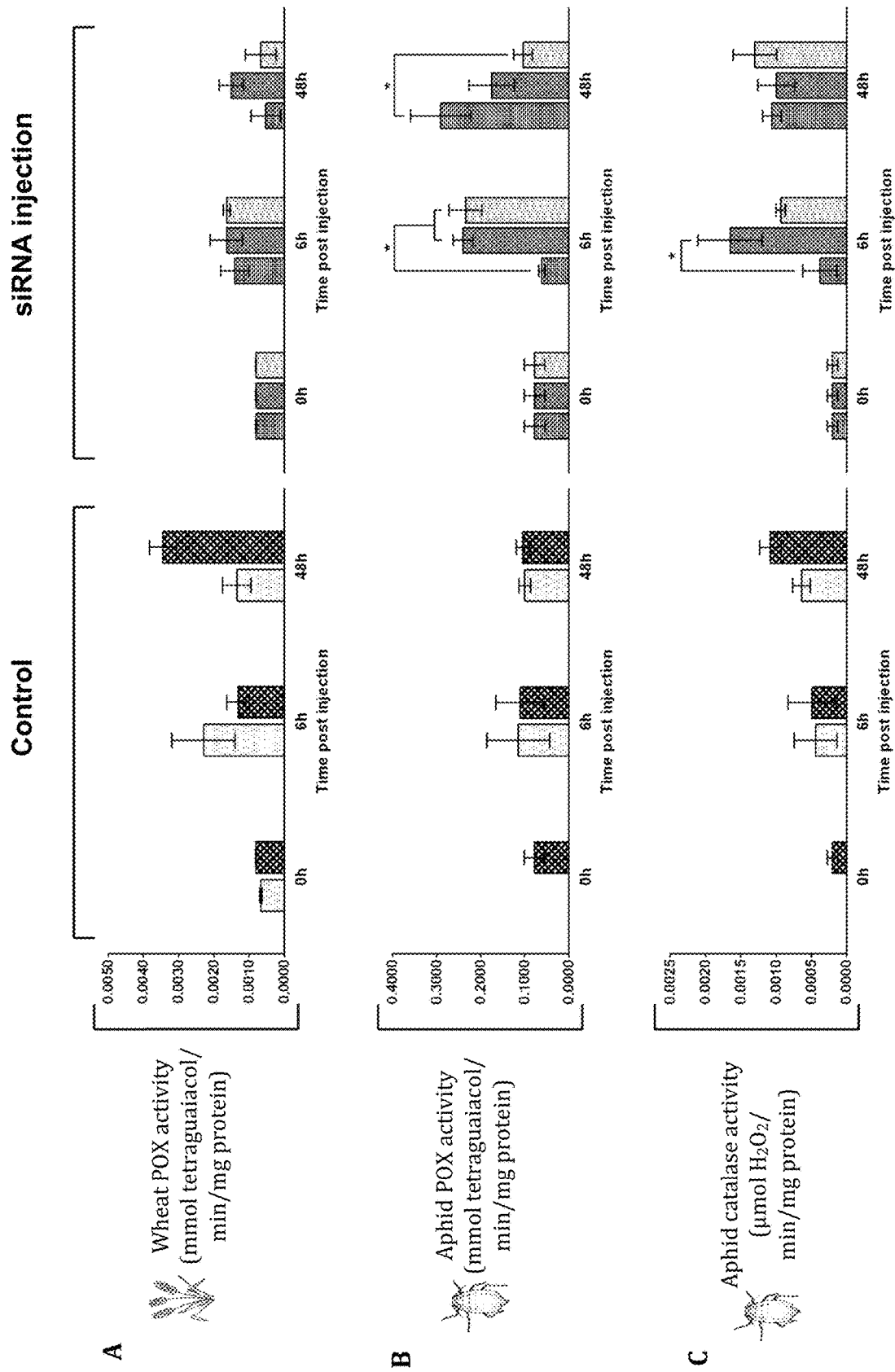

FIG. 17 (A) Catalase and (B) peroxidase activity of *D. noxia* biotype SAM after feeding on wheat leaves injected with cprr1-8- or c002-siRNA respectively. siRNA was dissolved in 10 mM Tris (pH 7.0) before injection. ▢ GamS, *D. noxia* susceptible wheat cultivar 'Gamtoos-S'; ▨ GamR, *D. noxia* resistant wheat cultivar 'Gamtoos-R'; ▩ No injection, wheat leaves without injection; Buffer, 10 mM Tris (pH 7); ▨ c002-siRNA, siRNA targeting c002 dissolved in 10 mM Tris (pH 7);  cprr1-8-siRNA, siRNA targeting cprr1-8 dissolved in 10 mM Tris (pH 7).

FIG. 18 Methylation patterns of Dncprr1-8. Bisulfite sequencing was used to determine the position and amount of 5-methylcytosine compared to unmethylated cytosine of *D. noxia* biotype SAM and SA1. Coverage of the 3' region of the gene was low and thus presence of methylation could not be determined. A higher frequency of methylation is observed in the exonic/coding domain regions.

FIG. 19 Dncprr1-8 cDNA sequence (SEQ ID NO: 3) that will be inserted into the monocotyledon RNA interference vector, p9-Ubi-RNAi2.

Figure 20:
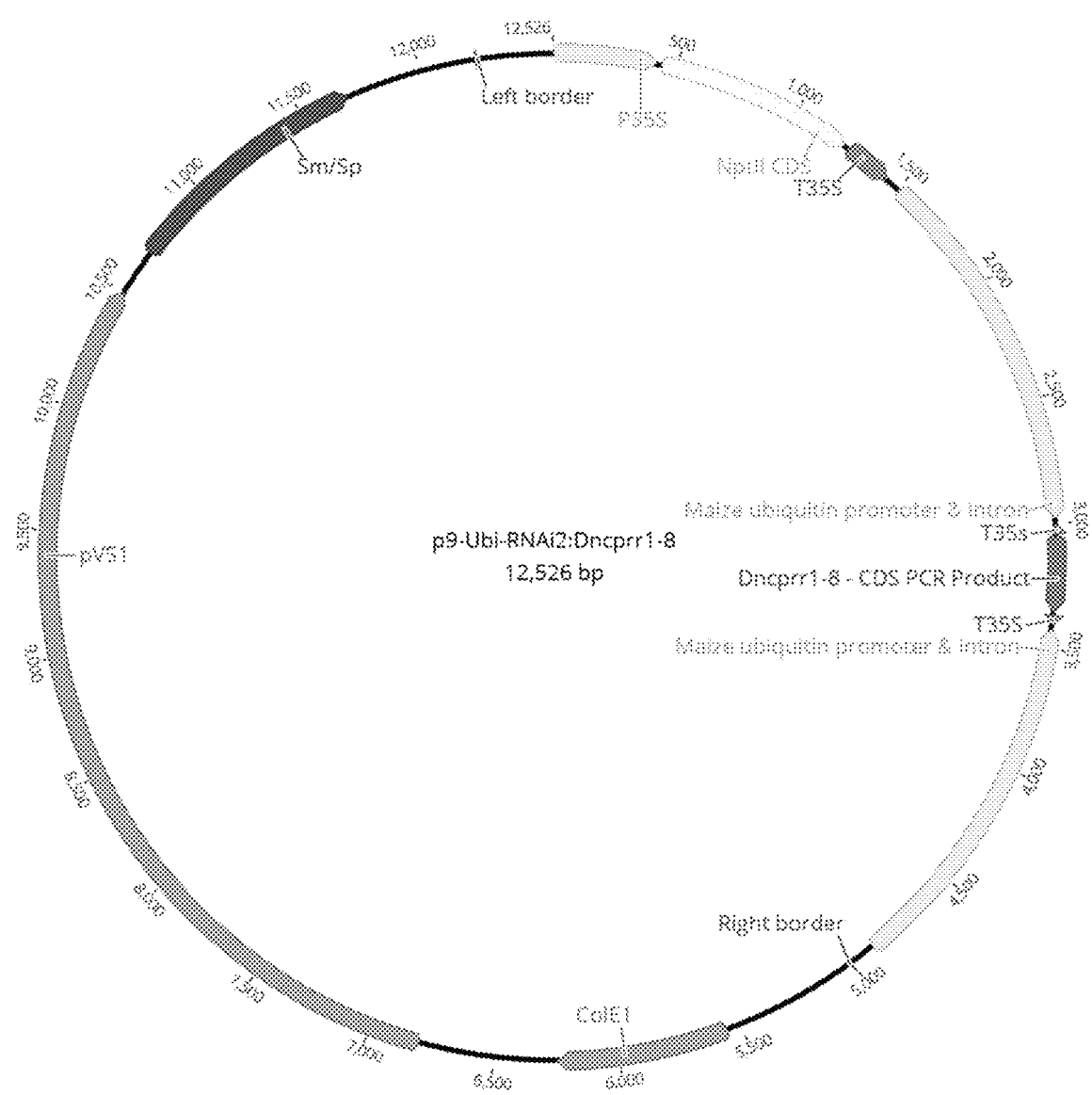

FIG. 20 Graphic representation of the binary RNA interference vector, p9-Ubi-RNAi2 containing Dncprr1-8 mRNA sequence. The inserted Dncprr1-8 sequence is flanked by two promoters which will result in the transcription of both strands of the inserted sequence.

DETAILED DESCRIPTION OF THE INVENTION siRNA molecules and their uses for controlling pest infestation are described herein. The siRNA molecules target the mature mRNA of *D. noxia* cprr1-8 in a region between about nucleotides 464 and 774 of SEQ ID NO: 23, or an equivalent region of an ortholog of *D. noxia* cprr1-8. The siRNA molecules are effective in suppressing the *D. noxia* cprr1-8 gene or an ortholog thereof, and ingestion of the siRNA molecules by a pest with this protein inhibits the biological activity of the pest. The use of the siRNA molecule is a natural and environmentally friendly method for controlling insect pests.

The region targeted by the siRNA molecule is generally a contiguous sequence of at least 19 nucleotides and up to about 25 nucleotides.

More particularly, the targeted region is between nucleotides 485 and 720 of SEQ ID NO: 23, and in one embodiment the target region is from nucleotides 486 to 508. In another embodiment the target region is between about nucleotides 509 and 720 and in yet another embodiment the target region is between about nucleotides 464 and 774.

A siRNA molecule according to the present invention will preferably comprise a double stranded RNA molecule, whose antisense strand will comprise an RNA sequence substantially complementary to the target region, and whose sense strand will comprise an RNA sequence complementary to the antisense strand, wherein both strands are hybridised by standard base pairing between nucleotides.

Within the meaning of the present invention, "substantially complementary" to a target mRNA sequence may also be understood as "substantially identical" to the target sequence. "Identity" as is known by one of ordinary skill in the art, is the degree of sequence relatedness between nucleotide sequences as determined by matching the order and identity of nucleotides between sequences. In one embodiment the antisense strand of an siRNA having 85%, 86%, 87%, 88%, 89%, 90%, 91%, 92%, 93%, 94%, 95%, 96%, 97%, 98% or 99% complementarity to the target mRNA sequence is considered substantially complementary and may be used in the present invention. The percentage of complementarity describes the percentage of contiguous nucleotides in a first nucleic acid molecule that can base pair in the Watson-Crick sense with a set of contiguous nucleotides in a second nucleic acid molecule. In one embodiment, the antisense siRNA strand is 100% complementary to the target mRNA sequence, and the sense strand is 100% complementary to the antisense strand over the double stranded portion of the siRNA.

In one embodiment, the siRNA molecule comprises a polynucleotide which has at least 80%, 85%, 90%, 95% or 100% sequence identity to the sequence 5' UAAACAAUCGCAAGAAGCUGA 3' (SEQ ID NO: 1) and a polynucleotide which has at least 80%, 85%, 90%, 95% or 100% sequence identity to the sequence 5' AGCUUCUUGCGAUUGUUUAAG 3' (SEQ ID NO: 2).

The siRNA molecule can consist of the duplex:

```
                                        (SEQ ID NO: 1)
       5' UAAACAAUCGCAAGAAGCUGA 3'

(SEQ ID NO: 2)
       5' AGCUUCUUGCGAUUGUUUAAG 3'.
```

Isolated polynucleotides or sets of polynucleotides encoding an siRNA molecule as described above are also provided in this invention. One example is a polynucleotide comprising a sequence which has at least 80% identity to SEQ ID NO: 3. More particularly, the polynucleotide may have at least 85% identity to SEQ ID NO: 3, at least 90% identity to SEQ ID NO: 3 or at least 95% identity to SEQ ID NO: 3. In one embodiment, the polynucleotide is identical to SEQ ID NO: 3.

In the context of the present invention, the expression "at least 80% identity" refers to a sequence identity of at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to the respective reference polynucleotide. Preferably, the polynucleotide in question and the reference polynucleotide exhibit the indicated sequence identity over a continuous stretch of 19, 20, 25, 30, 40, 50, 60, 70, 80, 90, 100, 150, 200 or more nucleotides.

A vector encoding the siRNA molecule as described above is further provided. The vector can include a polynucleotide as described above.

Methods are known in the art for administering the siRNA molecule to pests. For example, the siRNA molecule can be injected into or caused to be ingested by the pest. Ingestion can occur by feeding the pest with an artificial food containing the siRNA molecule, by causing a plant to transiently or stably express the siRNA molecule, by injecting a plant with the siRNA, or by applying the siRNA molecule to a surface of the plant, such as by spraying the siRNA molecule onto the plant. In one embodiment of the invention, plants or plant cells are transformed with a polynucleotide or set of polynucleotides encoding the siRNA molecule, so as to produce a transgenic plant which expresses the siRNA molecule. In another embodiment, a composition comprising the siRNA molecule is sprayed onto the plant. The composition can be a pesticide.

Vectors comprising a polynucleotide which can cause a transformed host to express RNA which subsequently becomes the siRNA molecule are also provided, as are plants and plant cells transformed with a polynucleotide encoding the siRNA molecule.

The siRNA molecule can be used to control pest infestation, improve crop yield or produce a commodity product.

When the siRNA molecule is ingested by a pest which feeds on the crop, or when the siRNA molecule is otherwise administered to the pest, the biological activity of the pest may be altered, and in particular the fitness or virulence of the pest may be reduced. For example, the survival rate of the pest may be decreased or its reproduction abilities may be reduced. This may be as a result of a target gene in the pest being suppressed. For example, the target gene can be the cprr1-8 gene.

In one embodiment, the siRNA molecule of the invention is used to control *Diuraphis noxia*. However, a person skilled in the art will understand that the siRNA molecule could also be used to control other crop pests, such as other aphid species (e.g. *Aphis fabae, Aphis glycines, Brevicoryne brassicae, Aphis gossypii, Macrosiphum euphorbiae, Acyrthosiphon pisum, Dysaphis plantaginea, Aphis craccivora, Myzus persicae, Schizaphis graminum, Rhopalosiphum padi, Rhopalosiphum maidis, Sitobion avenae*), other Hemipteran (e.g. whitefly) or other insects (e.g. *Thrips*, Lepidoptera larva, Diptera larva, Coleoptera larva, Tetranychidae, Gryllidae and Caelifera).

Means to identify orthologous genes and target sequences are available to a person of skill in the art and comprise the use of BLAST searches and database mining of databases such as the EMBL, NCBI and other databases comprising polynucleotides and amino acid sequences.

The *Myzus persicae* larval cuticle protein cprr1-8 ortholog is one example. In a study conducted by the inventors, siRNA molecules targeting the nucleotides CAGAAACCAGAAGACUCCAAAAA (SEQ ID NO: 43) of the *M. persicae* larval cuticle protein cprr1-8 were synthesized. The siRNA molecule comprised polyribonucleotide strands GAAACCAGAAGACUCCAAAAA (SEQ ID NO: 44) and UUUGGAGUCUUCUGGUUUCUG (SEQ ID NO: 45). When ingested by *M. persicae*, this siRNA caused a significant reduction in nymph production (data not shown).

In one embodiment of the invention, the plants which are injected or sprayed with the siRNA molecules, or transformed to express the siRNA molecules, are wheat plants. A person skilled in the art, however, will understand that the invention is not intended to be limited to the introduction of the siRNA molecule into wheat plants, and that other plants could also be transformed with the siRNA. For example, other suitable plants include crop plants such as barley, sugarcane, maize, rice, rye, sorghum, soya, palm, potato, cassava, sugar beet, banana, citrus, grapes, apple, watermelon, mango, cucumber, tomato, brassica species like rapeseed, other vegetables, tea, coffee, tobacco, cannabis, cotton and ornamental plants such as roses.

In the context of the present invention, the term "virulence" refers to the ability of an insect to feed and proliferate on a particular plant.

In higher organisms, reactive oxygen species (ROS) are regularly generated by mitochondrial electron transport, when partially reduced and highly reactive metabolites of $O_2$ such as superoxide anion ($O_2^-$) and hydrogen peroxide ($H_2O_2$) are formed during cellular respiration. Excessive release of ROS damages lipids, proteins, and DNA, which leads to oxidative stress, loss of cell function, and programmed cell death. ROS are also actively released by hosts, in response to cellular invasion by pathogens as first line of defense, and occur in all eukaryotic cells. To regulate oxidative stress, the eukaryotic cell produces different ROS-scavenging enzymes, such as superoxide dismutase (which reduces $O_2^-$. to $H_2O_2$), glutathione peroxidase and catalase (which reduces $H_2O_2$ to $H_2O$).

This happens in both the host plant and insect species. An increase in peroxidase activity also occurs in wheat after *D. noxia* infestation, which is indicative of the activation of systemic acquired resistance (SAR), albeit the induction is delayed in susceptible varieties.

The most virulent South African biotype of *D. noxia* is SAM (South African Mutant). This biotype was developed from biotype SA1 (the least virulent SA biotype, only virulent to dn3) by feeding it aphid-resistant wheat cultivars, thus placing it under continuous selection pressure. As a result, SAM has been shown to express virulence against all described Dn genes found in wheat (SAM avoids detection by its host plant during feeding and a limited increase in peroxidase activity and SAR is measured). This characteristic makes biotype SAM a useful model in studies to elucidate the mechanism of virulence against resistance genes.

Arthropod cuticle is a composite, bipartite system, made of chitin filaments embedded in a proteinaceous matrix, which serves as a protective barrier, and provide structural and mechanical support. The physical properties of cuticle are determined by the structure and the interactions of its two major components, which are cuticular proteins (CPs) and chitin. The proteinaceous matrix consists mainly of structural CPs, while the majority of these belonging to the CPR family, containing a conserved R&R region (Rebers and Riddiford Consensus). Two major subfamilies of the CPR family (i.e. RR-1 and RR-2) have been identified from conservation at sequence level and some correlation with the cuticle type.

The RR1 protein, which can be isolated from the salivary gland, is unique to the biotype SAM. It is encoded by the cprr1-8 gene. The function of RR1 during aphid feeding was investigated to determine whether this protein is associated with the virulence of SAM. This was done using RNA interference (RNAi)-mediated gene silencing or knock-down.

The RNAi process relies on double-stranded RNA (dsRNA) precursors, specifically lowering transcript abundance of a target gene when introduced into cells. The process involves the cleavage of the dsRNA precursors into siRNA (~21-23 nucleotides in size) by the enzyme Dicer-2 (Dcr-2). The resulting siRNAs are then incorporated into an RNA-induced silencing complex (RISC). Argonaute-2 (Ago-2), the catalytic component of RISC, uses one of the siRNA strands as a template to recognize and degrade the complementary mRNA.

Although the siRNA molecules in one embodiment contain nucleotide sequences that are fully complementary to nucleotides CUUAAACAAUCGCAAGAAGCUGA of the mature *D. noxia* larval cuticle protein cprr1-8 (SEQ ID NO: 23, FIG. 9), it will be apparent to a person skilled in the art that 100% sequence complementarity between the siRNA and the target nucleic acid is not required to practice the invention. In order for a siRNA to effectively target a region, up to 2 nucleotides of the siRNA can be changed. The length of the siRNA (in which case it is simply referred to as dsRNA) can be increased according to the *D. noxia* larval cuticle protein cprr1-8 conserved sequence (italicized in FIG. 9, nucleotides 465-773). The siRNA could also target other areas of the *D. noxia* larval cuticle protein cprr1-8 conserved cuticle protein sequence, for example the Rebers and Riddiford chitin binding domain (double-underlined in FIG. 9, nucleotides 510-719). In the examples provided herein, the siRNA strands have a 3' overhang of two nucleotides. However, a person skilled in the art will understand that the length of the overhang can be varied (e.g. three nucleotides).

In some embodiments, siRNAs have 5'-phosphate and 3'-hydroxyl groups.

An important issue with siRNA molecules is their instability in biological fluids due to the ubiquitous nature of RNAses. Consequently, the use of many different chemical modifications to nucleotides has been described with the purpose of enhancing compound stability.

Thus, in an embodiment of the invention, the siRNA further comprises at least one nucleotide with a chemical modification. Preferred chemical modifications which enhance stability and reduce immunogenic effects include 2'-O-methyl nucleotides, 2'-fluoro nucleotides, 2'-amino nucleotides, 2'-deoxy nucleotides, or nucleotides containing 2'-O or 4'-C methylene bridges. Others preferred chemical modifications for exonuclease protection include ExoEndo-Light (EEL): modification of all pyrimidines in the sense strand to 2'-O-methyl residues, and modifications of all pyrimidines in a 5'-UA-3' or 5'-CA-3' motif in the antisense strand. In addition, position 1 of the sense strand can also be changed to 2'-O-methyl, preventing 5'-phosphorylation of the sense strand and thus increasing specificity of the siRNA by further inactivating the sense strand. In addition, the sense strand can also include a 2'-O-methyl modification in position 14, because 2'-O-Me at this position further inactivates the sense strand and therefore increases specificity of the siRNAs. Other preferred chemical modifications for exonuclease protection include Methyl-Fluoro (MEF): exo protection alternating 2'-fluoro and 2'-O-methyl modifications starting (5'-end) with a 2'-F on the sense strand and starting with 2'-O-Me on the antisense strand. In addition, position 1 of the sense strand can also be changed to 2'-O-Me and position 1 of the antisense strand to 2'-F (as this can efficiently be 5'-phosphorylated). Also, modification of the ribonucleotide backbone connecting adjacent nucleotides can be made by the introduction of phosphorothioate modified nucleotides. A further preferred chemical modification within the meaning of the present invention relates to the substitution of uracyl ribonucleotides with deoxythymidine (deoxyribonucleotides). In another embodiment of the present invention, at least one chemically modified nucleotide is on the sense strand, on the antisense strand or on both strands of the siRNA.

siRNA molecules of the invention can be synthesized by standard methods known in the art, e.g. by use of an automated synthesizer. RNAs produced by such methodologies tend to be highly pure and to anneal efficiently to form siRNA duplexes. Following chemical synthesis, single stranded RNA molecules are deprotected, annealed to form siRNAs, and purified (e.g. by gel electrophoresis or HPLC). Alternatively, standard procedures may be used for in vitro transcription of RNA from DNA templates carrying RNA polymerase promoter sequences. The sense and antisense transcripts may be synthesized in two independent reactions and annealed later, or may be synthesized simultaneously in a single reaction.

Three siRNA delivery techniques were attempted and compared: direct injection of dsRNA or siRNA into aphid haemolymph; feeding of dsRNA from an artificial diet; and plant-mediated RNAi to initiate down-regulation of gene targets. However, because aphids are so small (>3 mm in size), microinjection requires specialized equipment. Wheat also has a large genome (17 000 MB) and unlike Arabidopsis, can be cumbersome to transform. Thus, alternative strategies to achieve RNAi-mediated gene silencing in *D. noxia* were required for the experimental purposes of this invention, and a novel siRNA delivery method was developed—the siRNA was injected into leaves of wheat plants and aphids were subsequently fed on these wheat plants. This method allows observation of the interaction of plant and aphid during a gene silencing experiment, while this is not the case for siRNA/dsRNA delivery through artificial media. It is also not invasive like direct injection of siRNA or dsRNA into the aphid hemolymph and is less laborious than plant transformation if elucidating gene function is the immediate goal.

The siRNA of the present invention was shown to decrease foundress survival by approximately 50% and affected nymph production significantly during in planta feeding experiments. The present study also demonstrated transgenerational knockdown, in that expression of the Dncprr1-8 gene in the newly born embryos was decreased, making this method highly useful and feasible.

siRNA molecules may also be formed within a cell by transcription of RNA from an expression construct introduced into the cell. The expression constructs for in vivo production of siRNA molecules comprise siRNA encoding sequences operably linked to elements necessary for the proper transcription of the siRNA encoding sequence(s), including promoter elements and transcription termination signals. The siRNA expression constructs can further comprise vector sequences that facilitate the cloning of the expression constructs.

For example, in order to deliver siRNA to insect pests in a field scenario, crop plants will be transformed with a plant RNA interference vector containing cprr1-8 mRNA sequence. In particular, a cprr1-8 fragment of 301 bp in length (SEQ ID NO: 3, FIG. 19) can be amplified using high fidelity DNA polymerase from reverse transcribed mRNA and inserted into a binary vector, such as p9-Ubi-RNAi2 (FIG. 20) in the case of monocotyledons or p9U10-RNAi for dicotyledons. Wheat can thereafter be transformed with the constructed vector using agrobacterium. The transformed plant will produce RNA from both strands of the cprr1-8 fragment. The complementary RNA strands will anneal to form dsRNA which will be cleaved into siRNA in the plant cells. These siRNAs will be ingested when pest insects feed on the transformed crop plant. Based on the results described herein, this is expected to result in a reduction of fecundity and thus reduce the detrimental effect of insect pests.

Alternatively, the siRNA can be formulated into a suitable composition for use on plants. The composition can be suitably formulated to improve activity, stability and/or bio-availability and/or to limit toxicity. Formulations can contain biological salts, lipids or lipid derivatives, polysaccharides or polysaccharide derivatives, sugars or sugar derivatives, bio-friendly or approved GRAS additives.

The composition can be formulated in various types of formulations, such as solutions, wettable powders, soluble powders, tablets and water-soluble or dispersible granules. The composition can also be formulated as a concentrated stock (which is diluted in an aqueous solution prior to conventional spray application) or as a ready to use product.

A surfactant can be used as a wetting, solubilizing and penetrating agent. Suitable surfactants include peptide derived surfactants (i.e. surfactin and iturin), non-ionic surfactants, anionic surfactants and amphoteric surfactants, such as cholic acids, alkyl sulfate salts, alkylsulfonic acid salts, alkylarylsulfonic acid salts, alkyl aryl ethers and their polyoxyethylene derivatives, polyethylene glycol ethers, polyol esters and sugar alcohol derivatives.

Other components of the formulation can include additional surface active agents, solvents, cosolvents, dyes, U.V. (ultra-violet) protectants, antioxidants, antifoams, stickers, spreaders, anti-foaming agents, preservatives, humectants, buffers, carriers, emulsifiers, wetting agents, dispersants, fixing agents, disintegrators, acid solubilisers or other components which facilitate product handling and application.

These carriers, diluents, auxiliary agents and so forth are preferably selected to optimize the antifungal action on plants or plant material.

Solid carriers can include, for example, the following materials in fine powder or granular form: agarose/agar containing cell culture media or dried cell culture media; organic-type fertilisers; clays (e.g. kaolinite, diatomaceous earth, synthetic hydrated silicon oxide, Fubasami clay, bentonite, acid clay); talc and other inorganic minerals (e.g. sericite, quartz powder, sulfur powder, activated carbon, calcium carbonate); and chemical fertilizers (e.g. ammonium sulfate, ammonium phosphate, ammonium nitrate, ammonium chloride, urea). Liquid carriers can include, for example, cell culture media, water; alcohols (e.g. methanol, ethanol, isopropanol); ketones (e.g. acetone, methyl ethyl ketone, cyclohexanone); esters (e.g. ethyl acetate, butyl acetate); nitriles (e.g. acetonitrile, isobutyronitrile); and acid amides (e.g. dimethylformamide, dimethylacetamide), as well as dilute bases (e.g. sodium hydroxide, potassium hydroxide and amines).

Other auxiliary agents can include, for example, adhesive agents and dispersing agents, such as casein, gelatin, polysaccharides (e.g. powdered starch, gum arabic, cellulose derivatives, alginic acid, chitin), lignin derivatives and synthetic water-soluble polymers (e.g. polyvinyl alcohol, polyvinyl pyrrolidone, polyacrylic acid); salts (eg. citrate, chloride, sulphate, acetate, ammonium, bicarbonate, phosphate salts and like) and stabilizers such as PAP (isopropyl acid phosphate), BHT (2,6-di-tert-butyl-4-methylphenol), BHA (2-/3-tert-butyl-4-methyoxyphenol), vegetable oils, mineral oils, phospholipids, waxes, fatty acids and fatty acid esters.

One or more plant growth regulators, herbicides, fungicides, bactericides, insecticides, nematicides, acaricides, biochemical pesticides, plant produced pesticides (botanicals), antimicrobials, antifungals, plant nutrients and so forth can also be incorporated into the composition of the present invention.

The composition may be diluted in water, water organic mixture or with liquid carrier and sprayed or applied in controlled environments on the plant or plant material to be treated or used to wash plant materials or environment/systems/equipment or mixed with cell culture media or plant propagation media. Alternatively, the composition may be directly applied to the soil (in which the plant will be grown or is growing) with or without granular fertilizers or organic-type fertilisers for propagation of cultured plants or the improved growth of plants.

In accordance with the present invention, there may be employed conventional molecular biology, microbiology, and recombinant DNA techniques within the skill of the art. See, e.g., Sambrook, Fritsch and Maniatis, Molecular Cloning: A Laboratory Manual, 2nd ed., Cold Spring Harbor Laboratory Press, Cold Spring Harbor, N. Y., 1989 (herein "Sambrook et al., 1989"); DNA Cloning: A Practical Approach, Volumes I and II (Glover ed. 1985); Oligonucleotide Synthesis (Gait ed. 1984); Nucleic Acid Hybridization (Hames and Higgins eds. 1985); Transcription And Translation (Hames and Higgins eds. 1984); Animal Cell Culture (Freshney ed. 1986); Immobilized Cells And Enzymes (IRL Press, 1986); B. Perbal, A Practical Guide To Molecular Cloning (1984); Ausubel et al. eds., Current Protocols in Molecular Biology, John Wiley and Sons, Inc. 1994; among others.

Throughout the specification and claims, unless the contents requires otherwise, the word "comprise" or variations such as "comprises" or "comprising" will be understood to imply the inclusion of a stated integer or group of integers but not the exclusion of any other integer or group of integers.

The invention is described in more detail below in the following non-limiting examples.

EXAMPLES

Materials and Methods

Aphid Populations

Colonies of parthenogenetic (apterous) female aphids of South African *D. noxia* biotypes SA1 and SAM, expressing different levels of virulence, were separately established in BugDorm cages (MegaView Science Education Services Co. Ltd., Taiwan) in an insectary with the following conditions: 22.5±2.5° C., 40% relative humidity, and continuous artificial lighting from high pressure sodium lamps.

The aphid colonies were maintained on near isogenic wheat lines. SA1 was maintained on Tugela (*D. noxia* susceptible, biotype SA1), while SAM was maintained on TugelaDn 1, a wheat cultivar containing the Dn1 resistance gene. All cultivars were planted in sand-filled pots and watered daily with a fertilizer that consisted of 2 g Microplex (Ocean Agriculture (Pty) Ltd, South Africa), 164 g Sol-u-fert (Kynoch Fertilizers (Pty) Ltd, South Africa) and 77 ml potassium nitrate per 100 liters of water.

The c002 gene from *D. noxia* was used as reference in the present study.

Plant Material and Growth Conditions

Near isogenic wheat lines (NiLs), GamtoosR (GamR, resistant) and GamtoosS (GamS, susceptible) were grown under greenhouse conditions using natural lighting and kept at a temperature of 25° C.±2° C. The resistance in GamR was obtained after a 1RS/1BL translocation from rye (*Secale cereale* L.), and is denoted Dn7. GamR is known to express antixenosis and antibiosis against aphids during feeding. Antibiosis is observed when the plant reduces the reproductive fitness of aphids feeding on it, while antixenosis is the non-preference of a cultivar as host. Seeds were planted in pots filled with crusher dust and watered twice daily using drip irrigation. These plants were used for siRNA injection experiments. Plants used to maintain aphid colonies were grown under King Plus 800W LED lights for a 12 h photoperiod and at a temperature of 20° C.±1° C.

Sample Preparation and RNA Extraction

For RNA extraction of both aphid and plant material, samples were immediately flash-frozen in liquid nitrogen and ground in 1.5 ml Eppendorf tubes using a micropestle. RNA from aphids was extracted using an RNeasy Mini Kit (Qiagen) and on-column DNase I treatment (Qiagen) following the manufacturer's protocol. RNA from wheat was extracted by adding 600 μl TRI Reagent® (Zymo Research) to the ground material, after which the Direct-zol™ RNA MiniPrep Plus kit (Zymo Research) was used by following the manufacturer's protocol and stored at −80° C. until further use.

Complementary DNA (cDNA) synthesis was conducted using an iScript cDNA Synthesis Kit (Bio-Rad) according to the manufacturer's protocol. The quantity of the cDNA was assessed through Qubit analysis (Thermo Fisher Scientific; Central Analytical Services, CAF, Stellenbosch University), whereafter the cDNA was stored at −80° C. until further use.

Sequence Characterization of Gene Dncprr1-8 that Encodes the Protein RR1 from *Diuraphis noxia*

PCR primers were designed to amplify the transcript and genic area of Dncprr1-8 (Table 1). Synthesized cDNA was used as template for the amplification of transcript sequence and extracted DNA as template for the amplification of genes. The PCR products were purified using the MinElute Reaction Cleanup Kit (Qiagen) and Sanger sequenced at Central Analytical Services (CAF), Stellenbosch University. The PCR products of primers cprr1-8_gene_2 F and cprr1-8_gene_2 R (Table 1) were cloned before plasmids were Sanger sequenced.

Both ends of the raw reads were then trimmed in Geneious 9.1.8 (Biomatters, New Zealand) using the Trim Ends function which trims vector sequence (not required in the case of direct sequencing of PCR products), primer sequence and low quality sequence (error probability set 0.01). The Geneious assembler was used to assemble the trimed reads de novo at the highest sensitivity, after which it was aligned to the next-generation sequencing (NGS) reference genome sequence of biotype SAM using MUSCLE 3.8 (Edgar 2004).

The obtained sequences were submitted to the basic local alignment search tool (BLASTn and BLASTx) at the National Centre for Biotechnology Information (NCBI) (//blast.ncbi.nlm.nih.gov/Blast.cgi) to confirm the identity of genes Dncprr1-8 (FIGS. 4 and 9) and Dnc002. The protein coding region was analyzed for amino acid content through the use of the Geneious (v7.1.5) platform. Secondary protein structure was determined using the EMBOSS 6.5.7 tool gamier. To predict tertiary protein structure the Phyre2 web portal was used.

TABLE 1

Sequence of primers used for sequence verification and gene expression analysis of cprr1-8 and c002

| Name of primer | Sequences of primers (5'-3') | Template | Amplicon length (bp) | Annealing temp. (° C.) |
|---|---|---|---|---|
| c002 qPCR F | CCCGTATGAGAAGCCGACTG (SEQ ID NO: 26) | cDNA | 123 | 60 |
| c002 qPCR R | CCATCTTGGTGGGAGCTCTG (SEQ ID NO: 27) | cDNA | | |
| cprr1-8 CDS F | TTACTACCCAGGTGCCCCA (SEQ ID NO: 28) | cDNA | 434 | 59 |
| cprr1-8 CDS R | CTGTGGTTGGGAGGCGATTA (SEQ ID NO: 29) | cDNA | | |
| cprr1-8 qPCR F | CCCATCCAACCAAGCCTA (SEQ ID NO: 8) | cDNA | 123 | 56 |
| cprr1-8 qPCR R | TAGTATCCTTGTTGTCCCGG (SEQ ID NO: 10) | cDNA | | |
| cprr1-8_gene_1 F | GCATCAGTTGTGTCATTTGTCCA (SEQ ID NO: 30) | DNA | 1765 | 57 |
| cprr1-8_gene_1 R | GTTTGGGCCGTTTCAGCG (SEQ ID NO: 31) | | | |
| cprr1-8_gene_2 F | TCGTACTTTATCATACACTTATGAATT (SEQ ID NO: 32) | DNA | 1141 | 58 |
| cprr1-8_gene_2 R | GCGGGTCTCTATTTCTCAAT (SEQ ID NO: 33) | | | |

Design of siRNA

Once the sequence identities of the respective genes were confirmed, siRNAs targeting the Dncprr1-8 and Dnc002 were designed. (Table 2) These siRNAs have a 19 nt duplex region and a 2 nt 3'-overhang. The synthesized siRNA was obtained from IDT (https://www.idtdna.com/).

TABLE 2

Sequences of siRNAs

| Name of siRNA | Sequence of sense (5'-3') | Sequence of antisense (5'-3') |
|---|---|---|
| c002-siRNA | AUUUCAGAGAGACAUCGGAGG (SEQ ID NO: 34) | UCCGAUGUCUCUCUGAAAUUG (SEQ ID NO: 35) |
| cprr1-8-siRNA | UAAACAAUCGCAAGAAGCUGA (SEQ ID NO: 1) | AGCUUCUUGCGAUUGUUUAAG (SEQ ID NO: 2) |

Aphid Feeding on siRNA-Containing Artificial Media

An artificial feeding media developed specifically for *D. noxia* was used for aphid feeding. It was modified to contain the following: 0.10 g L-methionine (Merck), 0.20 g L-leucine (Sigma-Aldrich), 0.10 g L-tryptophan (Merck), 20.00 g sucrose (Merck), 0.20 g $MgCl_2 \cdot 6H_2O$ (Merck), and 0.25 g $K_2HPO_4$ (Sigma-Aldrich). The pH was adjusted to 7.0 using KOH (Merck) and $ddH_2O$ was added to a final volume of 100 ml. The media was then filter sterilized (0.2 μm pore size) and stored at 4° C.

Adult *D. noxia* of between 350 μm and 500 μm in size were placed individually inside a glass test tube with a 14 mm outside diameter. Parafilm M (Bemis, Oshkosh, WI, USA) was stretched close to its maximum capacity and placed over the opening. One microliter of siRNA (25 μg/μl) dissolved in RNase-free water (Ambion), or water for the control, was added to 24 μl artificial feeding media and placed on the stretched Parafilm M. Another layer of Parafilm M was then placed over the artificial media, spreading the media between the two layers. The test tubes were placed vertically in a stand with the open end at the bottom. Yellow tape was placed below the test tubes to encourage the aphids to feed. The experiment was repeated ten times (n=10) for each siRNA (i.e., Dnc002 and Dncprr1-8) and control (only media). The survival rate and the number of nymphs produced by each foundress were determined daily for four days.

Aphid Feeding on siRNA-Injected Wheat

The leaves of 30-day-old wheat plants were injected with 1 μl of 1 μg/μl siRNA dissolved in 10 mM Tris (Sigma-Aldrich) pH 7.0, at two locations in the midvein±5 mm apart, resulting in a total of 2 μg siRNA injected into each leaf. 10 mM Tris (Sigma-Aldrich) at pH 7.0 was injected as a control. A 10 μl, model 1701 Hamilton syringe with a 25.4 mm needle of 34 gauge, and 45° tip (Hamilton) was used for the injections. To contain aphids at the injection site, 15 ml polypropylene tubes (Greiner) were cut 45 mm from the opening, after which the closed end of the bottom tube was also removed to produce two tubes of ±45 mm in length. After 15 adult aphids were placed on the leaf between the injection sites, the leaf was threaded though the modified polypropylene tube, which was then held in place by cotton wool inserted at the top and bottom of the leaf at each end of the tube. The cotton wool was adjusted to allow aphids to move around freely within a ±25 $mm^2$ area centered around the injection sites. The cages were supported by wire wrapped around the tubes, and anchored to a wooden rod.

The foundress aphids were then allowed to feed for a period of 6 h or 48 h before the survivors were counted and sampled for further analysis. Leaf samples were taken at the same time points (6 h and 48 h), as well as directly after injection (0h). The experiment was performed in triplicate for every time point, and repeated twice over time (n=18).

Foundress Survival and Nymph Reproduction

Aphid reproductive measurements were taken. Directly after injection of siRNA, the aphids (n=15) (biotype: SAM) were caged on the emerged third leaf of each plant, with each plant considered a biological repeat, with thee biological repeats per treatment (n=3). As the siRNA titer only lasts for a limited time period, the mothers were considered the foundress, and her nymph production recorded from the second day of settlement (24 h). Aphid nymph numbers were measured daily and the mean total number of nymphs was calculated as a measure of fertility (n=15).

Gene Expression Analysis in Aphids Using qPCR

Silencing/knockdown of candidate genes was confirmed via qPCR. Primers were all designed to be 20 bp in length, to amplify a product of 123 bp in size and bind to the coding domain sequences of the Dnc002 and Dncprr1-8 genes. cDNA was synthesized as described, of which 0.5 ng was subsequently used for qPCR analysis. The qPCR setup comprised 5 μl SsoAdvanced Universal SYBR® Green Supermix (Bio-Rad) and one of the following primer sets: 0.5 μM of both the forward and reverse sets specific to Dnc002 or Dncprr1-8, 0.4 μM forward and 0.6 μM reverse specific to L32 or 0.6 μM of both the forward and reverse specific to L27 in 10 μl total volume reactions. The PCR cycling profile consisted of two initial steps of 50° C. for 1 min and 95° C. for 5 min, followed by 40 cycles at 95° C. for 10 s, 20 s at annealing temp specified in Table 1 and 72° C. for 20 s. A melt curve was also performed at 0.5° C. increments every 5 s from 65° C. to 95° C. Relative expression was calculated using untreated aphids sampled at day 0 as the calibrator and normalized to ribosomal proteins L27 and L32.

siRNA Concentration in Wheat

A section of leaf material 10 mm in length, which included the two injection sites in the middle, was used for RNA extraction as described above. Stemloop primers specific to the synthetic siRNAs were designed. Each 20 μl cDNA synthesis reaction contained 3 mM $MgCl_2$, 0.5 mM of each dNTP, 30 μM random hexamer primers, 0.5 μM specific stemloop primer, 150 ng RNA template, 1 μl ImProm-II™ Reverse Transcriptase (Promega) and 4 μl ImProm-II™ 5× Reaction Buffer (Promega). 5 ng of the cDNA was used in each 10 μl qPCR reaction as well as 5 μl SsoAdvanced universal SYBR® Green supermix (Bio-Rad), 1 μM universal stemloop reverse primer and 1 μM specific forward primer (DnC002-siRNA F or RR1-siRNA F, Table 3). Thermal cycling was used to perform the reactions. 18S expression levels for each sample were determined in a 10 μl qPCR reaction consisting of 0.2 ng cDNA, 5 μl SsoAdvanced Universal SYBR® Green Supermix and 0.4 μM of both the forward and reverse primers. After an initial 3 min step at 95° C., 40 cycles of 95° C. for 10 s, 54° C. for 30 s and 72° C. for 30 s were followed to amplify the product. The concentration of the siRNAs was calculated relative to 18S expression.

TABLE 3

Sequences of primers used for reverse transcription and qPCR of siRNAs

| Name of primer | Sequences of primers (5'-3') |
|---|---|
| c002 siRNA SL RT | GTCGTATCCAGTGCAGGGTCCGAGGTAT TCGCACTGGATACGACCCTCCG (SEQ ID NO: 36) |
| c002 siRNA F | GCCACCATTTCAGAGAGACAT (SEQ ID NO: 37) |
| cprr1-8 siRNA SL RT | GTCGTATCCAGTGCAGGGTCCGAGGTAT TCGCACTGGATACGACCTTAAA (SEQ ID NO: 38) |
| cprr1-8 siRNA F | GCACAGCTTCTTGCGATTG (SEQ ID NO: 39) |
| Universal stemloop R | GTGCAGGGTCCGAGGT (SEQ ID NO: 40) |
| 18S RNA forward | TGCCTATCAACTTTCGATGG (SEQ ID NO: 41) |
| 18S RNA reverse | TGGATGTGGTAGCCGTTTCTC (SEQ ID NO: 42) |

Aphid Protein Assays

Aphids were ground in ice-cold 50 mM phosphate buffer (pH of 7.5), 1 mM phenylmethylsulfonyl fluoride and 1 mM dithiothreitol. The extract was centrifuged at 4° C. for 15 min at 17 200 rpm. The supernatant was removed and kept on ice until protein assays were performed.

Catalase activity was determined colometrically by adding an aliquot of protein extract to 0.2 M phosphate buffer (pH 6.5) and 100 μM $H_2O_2$ and the degradation of $H_2O_2$ was observed at 260 nm. Enzyme activity was expressed as μmol $H_2O_2$·mg protein$^{-1}$·min$^{-1}$.

Peroxidase activity was measured by adding an aliquot of protein extract to 0.2 M phosphate buffer (pH 5.0), 100 mM $H_2O_2$ and 30 mM guaiacol. The formation of tetraguaiacol was a linear function of enzyme concentration and peroxidase activity was expressed as mmol tetraguaiacol min$^{-1}$·mg$^{-1}$ protein.

Wheat Protein Assays

Liquid $N_2$ was used to freeze wheat leaf material while it was ground. To this, 100 mM potassium phosphate (pH 7.5), 1 mM ethylenediaminetetraacetic acid and 1% polyvinylpyrrolidone was added to further homogenize the leaf material using a micropestle. The supernatant was collected after centrifugation at 4° C. for 15 min at 17 200 rpm.

Peroxidase activity was determined using horse radish peroxidase (BioLabs, Inqaba, Pretoria, ZA) as a standard. Hydrogen peroxide (0.06%) was added into a mixture containing 2 μg of leaf extract, 6 mM guaiacol, 25 mM potassium phosphate buffer (pH 6.0) and 24% distilled water. The formation of tetraguaiacol was a linear function of enzyme concentration and peroxidase activity was expressed as mmol tetraguaiacol min$^{-1}$·mg$^{-1}$ protein.

Aphid and Plant Protein Concentrations

All protein concentrations were determined using bovine serum albumin (Bio-Rad, USA) as standard and a Glomax spectrophotometer (Promega, USA) was used for this purpose.

DNA Methylation of Dncprr1-8

The DNA methylation state of D. noxia biotype SA1 and SAM was determined through whole genome bisulfite sequencing. DNA was extracted from at least 150 D. noxia biotype SA1 and SAM, respectively. The quality of DNA was assessed through Qubit 2.0 (Thermo Fisher Scientific) and a 2% (m/v) TAE agarose gel. The DNA samples were sent to Macrogen (South Korea) where the library preparation and sequencing was performed. After trimming and filtering the HiSeq X (Illumina, USA) reads obtained, Bismark was used to determine the methylation status of SA1 and SAM using the SAM genome as reference (GenBank assembly accession: GCA_001465515.1). For every cytosine in the reference genome Bismark outputs the amount of times it was methylated or unmethylated based on the bisulfite reads mapped to that position. It also distinguishes between the different contexts of cytosine (CpG, CHG and CHH) and the DNA strand that was methylated. In the present study this data set was manipulated to determine the proportion of methylation at every cytosine present in Dncprr1-8 which was then used to determine the total methylation in this gene and to graph the proportion of methylation at every site using Microsoft Excel (Microsoft).

Data Analysis

All sequence analysis was conducted utilizing the BLASTn and BLASTx tools and SWISSPROT with E-values lower than 1e-10 considered as significant. CutProtFam-Pred: Detection and classification of putative structural cuticular proteins from sequence alone, based on profile Hidden Markov Models was applied to confirm the RR1 protein identity (http://bioinformatics.biol.uoa.gr/CutProtFam-Pred) (Ioannidou et al., 2014) All statistical analyses were conducted by using GraphPad PRISM 7 Software Tools (www.graphpad.com/guides/prism/7/statistics/index.htm?usingstatistical_analysis_step_by_s.htm) with significance set at α=0.05. Aphid fertility measurements were calculated using the mean total number of nymphs born per day.

Results and Discussion

Sequence characterization of D. noxia Dncprr1-8

DNA Sequencing

Figure 3:
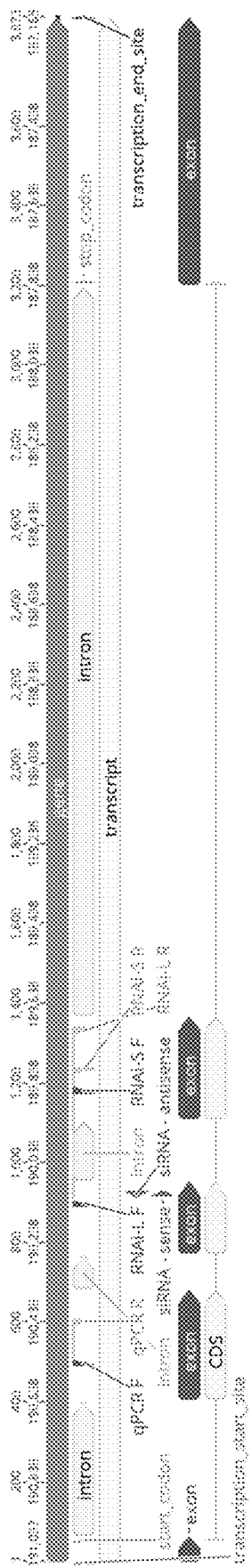
FIG. 3 Graphic view of the *Diuraphis noxia* cprr1-8 coding domain sequence, including annotations.

After obtaining the in silico predicted sequence for cuticle protein (RR-1) from the available SAM genome sequence (g3915.t2), 1663 bp of biotype SA1 and 1689 bp of biotype SAM were Sanger sequenced (SEQ ID Nos: 4 and 6, respectively). The initial Sanger reads of Dncprr1-8, generated using primers cprr1-8 gene_1 F and cprr1-8 gene_1 R, did not align properly to the reference SAM genome sequence (SEQ ID NO: 5) as there was a sequence gap in this reference sequence (FIGS. 1 and 2). Primers cprr1-8 gene_2 F and cprr1-8 gene_2 R were then designed on the initial Sanger reads obtained to close the sequence gap. As direct PCR sequencing was not possible, the fragments from primers cprr1-8 gene_2 F and cprr1-8 gene_2 R were cloned before it was sequenced. Analysis of the available sequences revealed that the Dncprr1-8 gene was 4197 bp long (SEQ ID NO: 7), containing 5 exons, a non-cytoplasmic domain and includes a 35-36 amino acid motif known as the chitin-binding Rebers and Riddiford (R&R) consensus (FIGS. 3 and 4). SAM clone #2 was found to be different to the SA1 clones. At base position 160 of the CDS, SAM clone #2 had a thymine instead of the guanine found in the other SA1 and SAM clones (SEQ ID NOS: 18 and 19). This should result in glycine to cysteine amino acid change. When predicted secondary structures of both G and T alleles were compared, the length of beta-strands was different and an additional coil was observed on the original G allele around the single nucleotide polymorphism (SNP) (FIG. 5). The predicted tertiary structures also differed between alleles (FIG. 6).

Complementary DNA Sequencing

The Sanger sequencing reads of biotype SA1 and SAM Dncprr1-8 transcripts (cDNA) almost covered the entire CDS. From the 826 bp in silico predicted Dncprr1-8 transcript, 718 bp from biotype SA1 and 730 bp from biotype SAM were Sanger sequenced directly form PCR products (FIGS. 7 and 8, SEQ ID Nos: 20 and 22). A C/T polymorphism was found at position 218 from the in silico predicted transcription start site. This polymorphism was present in both SA1 and in SAM and had no effect on amino acid sequence. No other polymorphisms were found between the two biotypes, based on cDNA sequencing.

Assessing the Relative Expression of Dnc002 and Dncprr1-8 in *D. noxia* Biotypes SA1 and SAM In order to assess whether there is any difference in the inherent expression of Dncprr1-8 and Dnc002 in biotypes SA1 and SAM when feeding on resistant (GamR) and susceptible (GamS) NiLs, the biotypes were fed on these lines for 10 days. After feeding for 10 days, qPCR expression analyses were conducted for Dncprr1-8 and Dnc002 and relative expression was calculated (FIG. 12). The obtained results revealed that even though the level of Dncprr1-8 expression was higher in SAM relative to its parent SA1, it was not statistically significant (FIG. 12B). While the expression of Dnc002 didn't differ between the aphid biotypes when feeding on GamS, although higher in SAM when feeding on GamR, this also wasn't statistically significant (FIG. 12A).

Optimizing siRNA of Dnc002 and Dncprr1-8

After determining that the relative expression of these genes didn't differ significantly in biotype SAM irrespective of its host, different siRNA delivery systems were compared. Firstly, siRNA was delivered through direct injection in the insect haemolymph. This technique proved impossible due to the size of the aphids. All the aphids died shortly after injection, irrespective of being injected with no fluid, buffer or siRNA (data not shown).

Delivery of the siRNA was then conducted using feeding on artificial media (Shakesby et al., 2009; Whyard et al., 2009) or in planta (feeding on siRNA injected plants (Lapitan et al. 2007)), whereafter reproduction and foundress survival (FIGS. 13 and 14) were assessed. The aphids were allowed to feed for 48 h before counting the number of nymphs produced to ensure settling of the foundresses. In the artificial feeding experiment, all foundresses survived irrespective of the feeding medium (FIG. 14). In contrast, 48 hours post injection (hpi) with Dncprr1-8-siRNA and Dnc002-siRNA, significantly more foundresses died after feeding on these plants than on any other treatment.

In the artificial feeding experiment, although not statistically significant, more nymphs were produced by foundresses feeding on artificial media containing Dncprr1-8-siRNA, than on just artificial medium or medium containing Dnc002-siRNA (FIG. 13). In planta knockdown with both Dncprr1-8-siRNA and Dnc002-siRNA resulted in significantly lower nymph production by foundresses feeding on these plants, when compared to foundresses feeding on GamS and buffer injected plants.

siRNA of Dnc002 and Dncprr1-8

To investigate the functions of Dnc002-siRNA and Dncprr1-8 in the salivary glands of virulent biotype SAM while feeding on one of the most RWA resistant wheat varieties, GamR (containing Dn7), biotype SAM was allowed to feed on uninjected, buffer injected and plants injected with either 2 µg Dnc002-siRNA (FIG. 15A) or 2 µg Dncprr1-8-siRNA (FIG. 15C) and relative gene expression measured. When biotype SAM fed on Dnc002-siRNA for 48 h, overexpression was observed relative to untreated and buffer injected leaves at 6 h and 48 h after introduction of aphids. Upregulation of Dnc002 was also observed when SAM fed on GamS.

At 6 h after aphid introduction, Dncprr1-8 expression measured in SAM differed according to the plants they fed on and was in the following order (from highest): uninjected GamR>buffer injected GamR>Dncprr1-8-siRNA>GamS. However, the Dncprr1-8 expression differed only statistically between aphids that fed on GamS, GamR and buffer injected plants (P≤0.05). At 48 hpi the expression of Dncprr1-8 in aphids feeding on GamS was significantly lower than that measured after 6 hpi, and also lower than in aphids feeding on Dncprr1-8-siRNA injected GamR plants. In fact, the levels of Dncprr1-8 of the latter aphids were comparable to those feeding on GamS and much lower than those feeding on uninjected GamR plants.

At 48 hpi the expression of Dncprr1-8 was the lowest in aphids feeding on Dncprr1-8-siRNA followed by GamS, buffer injected GamR and the highest expression was observed in aphids feeding on GamR. Although not significant, Dncprr1-8 expression was lower in both aphids that fed on Dncprr1-8-siRNA injected GamR and GamS at 48 hpi compared to 6 hpi. Between the same time points Dncprr1-8 expression of aphids that fed on buffer injected GamR also decreased, but not to the same extend as Dncprr1-8-siRNA injected plants and GamS. When feeding on GamR, Dncprr1-8 expression stayed roughly the same.

To validate that the response measured in the feeding aphids can be directly correlated to siRNA present in the plants, the levels of Dncprr1-8-siRNA and Dnc002-siRNA were quantified using stemloop primers and qPCR analyses to reveal the siRNA concentration relative to wheat 18S expression (FIGS. 15B and D). These results confirmed that Dnc002-siRNA and Dncprr1-8-siRNA were present in the siRNA injected leaves and absent from the untreated leaves. Six hours after injection the siRNA was still present at levels equivalent to levels measured directly after injection. After 48 h a decrease in siRNA was observed, although it was still present in significant quantities, indicating relative stability within the plant. The measured levels of siRNA were significantly higher (P≤0.05) in the Dncprr1-8-siRNA and Dnc002-siRNA injected plants, when compared to all other plants.

Transgenerational Effect of siRNA

To validate whether the interference also affects the unborn embryos of the feeding foundresses, newly born nymphs were sampled on 0, 96 and 144 hpi and assayed for the expression of Dncprr1-8 (FIG. 16). Interestingly, the effect of knockdown was most severe in newly born nymphs produced 96 hpi, and differed significantly from that in nymphs produced from foundresses feeding on uninjected GamR plants.

*D. noxia*-Host Interaction

To elucidate the functions of Dnc002 and Dncprr1-8 in the salivary glands of virulent biotype SAM during feeding on GamR (a wheat expressing antibiosis and antixenosis, biotype SAM was allowed to feed on uninjected, buffer injected and plants injected with either 2 µg Dnc002-siRNA or 2 µg Dncprr1-8-siRNA, whereafter the activities of reactive oxygen species (ROS) were assayed in the feeding aphids and host (FIG. 17).

As peroxidase (PDX) is a ROS enzyme and a marker of the oxidative burst during the host defense throughout the interaction of wheat and *Diuraphis noxia*, it was assayed at 0, 6 and 48 hpi (FIG. 17A). When comparing the PDX activity between uninjected, infested GamS and GamR plants, higher PDX activity was measured in the plants after infestation, with the highest PDX activity assayed in the GamR 48 hpi (P≥0.05), which is indicative of the induction of the host defense response. However, even though PDX activity increased slightly in the Dnc002-siRNA and Dncprr1-8-siRNA injected plants after 6 hpi, it decreased after 48 hpi to that at 0 h. This observation suggests that unlike aphids feeding on uninjected GamR plants, the aphids feeding on the Dnc002-siRNA and Dncprr1-8-siRNA injected plants were not perceived as invasive. Hence the decrease in the transcription of host defense proteins like PDX, as these are expected to increase as part of the systemic acquired resistance pathway in the resistant GamR plants and remained elevated to provide prolonged basal resistance.

Although aphid survival rate was still unaffected 6 h after feeding on siRNA (FIG. 14), PDX and catalase (CAT) activity increased in aphids feeding on uninjected GamS and GamR, buffer injected and Dnc002-siRNA or Dncprr1-8-siRNA injected plants over the 48 h period (FIG. 17B). However, PDX activity was only significantly higher in aphids feeding on Dnc002-siRNA or Dncprr1-8-siRNA injected plants (P≥0.05) 6 hpi (FIG. 17B). CAT activity was also elevated at 6 hpi in aphids that fed on Dncprr1-8- and Dnc002-siRNA injected plants, with CAT activity in Dnc002-siRNA fed aphids being significantly higher than in aphids that fed on buffer injected plants (P≥0.05) (FIG. 17C). ROS metabolism influences critical parameters of insect physiology, including fecundity and immune response. As PDX and CAT activity is indicative of cellular stress experienced in response to the aphids' feeding environment, the results suggest that both genes afford the aphids some level of "protection" while feeding on the antixenotic and antibiotic GamR, as partial knockdown of these genes decreased foundress survival by approximately 50% and affected nymph production significantly during in planta feeding experiments. In a field setting, a reduction of the aphid reproduction by 40-60% would dramatically decrease aphid population growth, contributing to a substantial reduction in agricultural losses.

DNA Methylation of Dncprr1-8

In order to determine if DNA methylation is involved in the differential expression of Dncprr1-8 between biotype SAM and SA1, whole genome sequence data of bisulfite treated DNA from at least one hundred aphids from each biotype was analyzed. In doing so the proportion of DNA methylation at every cytosine of Dncprr1-8 was determined for the two biotypes. Methylation was observed at more sites and at a higher frequency in SAM compared to SA1 in the CpG, CHG and CHH contexts (Table 4).

TABLE 4

DNA methylation of Dncprr1-8. The amount of cytosine sites and total proportion of methylation (5-methylcytosine) in the contexts of CpG, CHG and CHH is compared between SA1 and SAM Dncrpp1-8

| | Amount of sites methylated | | | | Percentage methylation | | | |
|---|---|---|---|---|---|---|---|---|
| | CpG | CHG | CHH | Total | CpG | CHG | CHH | Total |
| SA1 | 38 | 34 | 58 | 130 | 1.83% | 1.13% | 0.76% | 1.08% |
| SAM | 54 | 42 | 67 | 163 | 2.58% | 1.31% | 1.04% | 1.45% |

Methylation was mainly observed in the exonic areas of Dncprr1-8 (FIG. 18). At 416 bp, 422 bp, 433 bp and 436 bp after the TSS, SAM is methylated 90.00%, 95.24%, 95.65% and 95.65%, while SA1 was methylated at 78.57%, 73.68%, 82.35% and 82.35%, respectively. That amounts to a difference in the average methylation for those sites of 14.90%. At 518 bp after the TSS of Dncprr1-8 (second exon), SA1 is methylated at 27.3% while no methylation was observed in SAM even though 26 reads were mapped at that position. In the area of Dncprr1-8 that translates to the chitin-binding domain (1197-1274 bp from the TSS), the following observations were made: from 1,200 bp to 1,225 bp from the TSS (just left from the highest peak on the graph on the 4th exon as seen in FIG. 18), SAM is 2.13% more methylated than SA1. Furthermore, the highest frequency of DNA methylation in both biotypes was observed at 1268-1294 bp from the TSS.

REFERENCES

Edgar, R. C. (2004). MUSCLE: Multiple sequence alignment with high accuracy and high throughput. *Nucleic Acids Res.* 32, 1792-1797.

Lapitan, N. L. V., Li, Y.-C., Peng, J. and Botha, A-M. (2007) Fractionated extracts of Russian wheat aphid eliciting defense responses in wheat. *J. Econ. Entomol.* 100, 990-999.

Shakesby, A. J., Wallace, I. S., Isaacs, H. V., Pritchard, J., Roberts, D. M. and Douglas, A. E. (2009). A water-specific aquaporin involved in aphid osmoregulation. *Insect Biochem. Mol. Biol.* 39, 1-10.

Whyard, S., Singh, A. D. and Wong, S. (2009). Ingested double-stranded RNAs can act as species-specific insecticides. *Insect. Biochem. Mol. Biol.* 39, 824-832.

The invention claimed is:

1. An siRNA molecule targeting the mature mRNA of *Diuraphis noxia* (*D. noxia*) larval cuticle protein cprr1-8 (cprr1-8) in a region between nucleotides 464 and 774 of SEQ ID NO: 23, wherein the siRNA molecule includes a polynucleotide comprising an RNA sequence which is complementary to at least 19 contiguous nucleotides in the region between nucleotides 464 and 774 and the siRNA is capable of silencing the cprr1-8 gene in *D. noxia* and reducing virulence of *D. noxia* which are administered the siRNA molecule.

2. The siRNA molecule according to claim 1, wherein the region targeted by the siRNA molecule is a contiguous sequence of from 19 to 25 nucleotides.

3. The siRNA molecule according to claim 1, which targets the mature mRNA of *D. noxia* cprr1-8 in a region between nucleotides 485 and 720 of SEQ ID NO: 23.

4. The siRNA molecule according to claim 1, which targets nucleotides 486-508 of SEQ ID NO: 23.

5. The siRNA molecule according to claim 1, comprising a polynucleotide which has at least 80% sequence identity to the sequence 5' UAAACAAUCGCAAGAAGCUGA 3' (SEQ ID NO: 1) and a polynucleotide which has at least 80% sequence identity to the sequence 5' AGCUUCUUGCGAUUGUUUAAG 3' (SEQ ID NO: 2).

6. The siRNA molecule according to claim 1, comprising a polynucleotide which has at least 85% sequence identity to the sequence 5' UAAACAAUCGCAAGAAGCUGA 3' (SEQ ID NO: 1) and a polynucleotide which has at least 85% sequence identity to the sequence 5' AGCUUCUUGCGAUUGUUUAAG 3' (SEQ ID NO: 2).

7. The siRNA molecule according to claim 1, comprising a polynucleotide which has at least 90% sequence identity to the sequence 5' UAAACAAUCGCAAGAAGCUGA 3' (SEQ ID NO: 1) and a polynucleotide which has at least 90% sequence identity to the sequence 5' AGCUUCUUGCGAUUGUUUAAG 3' (SEQ ID NO: 2).

8. The siRNA molecule according to claim 1, comprising a polynucleotide which has at least 95% sequence identity to the sequence 5' UAAACAAUCGCAAGAAGCUGA 3' (SEQ ID NO: 1) and a polynucleotide which has at least 95% sequence identity to the sequence 5' AGCUUCUUGCGAUUGUUUAAG 3' (SEQ ID NO: 2).

9. The siRNA molecule according to claim 1, comprising a polynucleotide with the sequence 5' UAAACAAUCGCAAGAAGCUGA 3' (SEQ ID NO: 1) and a polynucleotide with the sequence 5' AGCUUCUUGCGAUUGUUUAAG 3' (SEQ ID NO: 2).

10. The siRNA molecule according to claim 1, which consists of the duplex:

```
                                   (SEQ ID NO: 1)
5' UAAACAAUCGCAAGAAGCUGA 3'

(SEQ ID NO: 2)
5' AGCUUCUUGCGAUUGUUUAAG 3'.
```

11. A method for controlling pest infestation, the method comprising:

(a) introducing an siRNA molecule targeting the mature mRNA of *D. noxia* cprr1-8 in a region between nucleotides 464 and 774 of SEQ ID NO: 23, into a plant or transforming the plant with a polynucleotide which causes the plant to express the siRNA molecule wherein the siRNA molecule includes a polynucleotide comprising an RNA sequence which is complementary to at least 19 contiguous nucleotides in the region between nucleotides 464 and 774 and the siRNA is capable of silencing the cprr1-8 gene; and (b) providing the plant, or portion thereof, to the pest;

(c) wherein pests to which the siRNA have been administered have reduced virulence.

12. A method for improving crop yield, the method comprising:

a) transforming the plant with a polynucleotide which causes the plant to express an siRNA molecule targeting the mature mRNA of *D. noxia* cprr1-8 in a region between nucleotides 464 and 774 of SEQ ID NO: 23, wherein the siRNA molecule includes a polynucleotide comprising an RNA sequence which is complementary to at least 19 contiguous nucleotides in the region between nucleotides 464 and 774 and the siRNA is capable of silencing the cprr1-8 gene; and b) cultivating the plant to allow expression of the siRNA molecules, wherein the expression inhibits feeding by a pest and loss of yield due to pest infestation.

13. The method according to claim 11, wherein the plant is selected from the group consisting of wheat, barley, sugarcane, maize, rice, rye, sorghum, soya, palm, potato, cassava, sugar beet, banana, citrus, grapes, apple, watermelon, mango, cucumber, tomato, brassica species, rapeseed, tea, coffee, tobacco, cannabis, cotton and ornamental plants.

14. The method according to claim 13, wherein the plant is wheat.

15. The method of claim 11, wherein the pest is an insect.

16. The method according to claim 15, wherein the insect is selected from the group consisting of *Diuraphis noxia, Myzus persicae, Aphis fabae, Aphis glycines, Brevicoryne brassicae, Aphis gossypii, Macrosiphum euphorbiae, Acyrthosiphon pisum, Dysaphis plantaginea, Aphis craccivora, Schizaphis graminum, Rhopalosiphum padi, Rhopalosiphum maidis, Sitobion avenae*, whitefly, *Thrips*, Lepidoptera larva, Diptera larva, Coleoptera larva, Tetranychidae, Gryllidae and Caelifera.

17. The method according to claim 16, wherein the insect is *Diuraphis noxia*.

18. The method according to claim 11, wherein the siRNA molecule targets the mature mRNA of *D. noxia* cprr1-8 in a region between nucleotides 485 and 720 of SEQ ID NO: 23.

19. The method according to claim 11, wherein the siRNA molecule comprises a polynucleotide comprising the sequence 5' UAAACAAUCGCAAGAAGCUGA 3' (SEQ ID NO: 1).

20. The siRNA molecule according to claim 1, wherein the SiRNA molecule comprises a polynucleotide comprising the sequence 5' UAAACAAUCGCAAGAAGCUGA 3' (SEQ ID NO: 1).

* * * * *

SEQUENCE LISTING

<160> NUMBER OF SEQ ID NOS: 45

<210> SEQ ID NO 1
<211> LENGTH: 21
<212> TYPE: RNA
<213> ORGANISM: Diuraphis noxia

<400> SEQUENCE: 1
uaaacaaucg caagaagcug a                                              21

<210> SEQ ID NO 2
<211> LENGTH: 21
<212> TYPE: RNA
<213> ORGANISM: Diuraphis noxia

```
<400> SEQUENCE: 2
agcuucuugc gauuguuuaa g                                              21

<210> SEQ ID NO 3
<211> LENGTH: 301
<212> TYPE: DNA
<213> ORGANISM: Diuraphis noxia

<400> SEQUENCE: 3
caaagtgcca gctatcctta acaatcgca agaagctgac ttgaacggat tcaaatacgg     60
atacgaaacc gaaaacggca tcgtcgccca ggctgctgga tacgttaaga acgccggttc    120
cgaaaacgcc gtccaagtga tcgaaggctc gtatgcctac atcggtgacg atggtgctcc    180
agtcgaagtc aagtactacg ctgacgagac cggttaccac gcagccggaa acgtcgtccc    240
gaccactccc ccagagatcg ccaagtcttt ggaattaatc gcctcccaac cacagaaacc    300
a                                                                    301

<210> SEQ ID NO 4
<211> LENGTH: 1663
<212> TYPE: DNA
<213> ORGANISM: Diuraphis noxia

<400> SEQUENCE: 4
ggtatacgtc caaaaaaatc accatgaaca ctttggtgag ttaaataata tttctttaaa     60
tcttcttaaa aaagacatag caatattatc attttatttt ttaatttagt tatacaacgc    120
attgtataat agtttcaatt tataaacagt ttaatttaaa gaaaaaatag tatarttact    180
gaaattattt attattttcg tactttatca tacacttatg aatttttagt attttttggta   240 tacgagaata tcttattatt ttataaatat cttataaaat aaatgctcat attatgttat    300
acttattttt taaattaatg aaactacgaa aaaattaatt ttaactcaaa ttttcaaatt    360
ttttaagttc aaataagtac ctcaatttat attatgaaca gtgtaaaagt ataatattta    420
cgtttactgc aaccattatt atattagaat cagtcttatt attttttgtac ttcataaaaa    480 aatgcctgaa aattaaaatt taaaagatat ctctacaatt taacgcatag gtaatcttat     540
taatcgtaat catattttaa ccaaatccat attttttagtt tcaatttaaa attgacatta    600
cacctgtaaa agttttcaca gtatatcttc acagcaaaaa atatgcataa aattatttct    660
ttcctcagca ctttatacaa ttttcgtgcc ttcgttttta ggtagtgtta gtagctgtca    720
tcgcagcggt gtctgctgcg gccccacctc aggaagctgc caaagctttt actttcagtg    780
gattcccatc caaccaagcc tactacccag gccaacaagg gtactaccca ggatacattg    840
gttaccaggg ttatcaaggt tacagcggat tccgtaatgg atactacccg ggacaacaag    900
gatactaccc aggataccaa ggttaccagg gatactaccc aggataccaa ggttaccagg    960
gatactaccc aggatatcaa ggtttaattt cgttaattat acgtctaaaa cactgcagag   1020
tcacatgatg tgttataagt ttcttataat ttactatttt cacataggtt acaaccgcgg    1080
ttactaccca ggtgccccag ccgtctaccc caccgtcacc cccgccccaa tcatcgcacc    1140
agtgccagtc gcgcccaagg ctgtttctcc agtgtacaaa cccgtagaca acaaagtgcc    1200
agctatcctt aaacaatcgc aagaagctga cttgaacgga ttcaaatacg gttagtatt    1260 ataattggta cattattatt cgatcggttt tctgcatcac agcgaatggy ggattaaaat    1320
tgagaaatag agaccgcgc caaatggcat gtccacaaaa aatacattgt ttgtaaataa    1380
cggatatatt tgtgtgcatt ttcagatacg aaaccgaaaa cggcatcgtc gcccaggctg    1440
```

```
ctggatacgt taagaacgcc ggttccgaaa acgccgtcca agtgatcgaa ggctcgtatg    1500
cctacatcgg tgacgatggt gctccagtcg aagtcaagta ctacgctgac gagaccggtt    1560
accacgcagc cggaaacgtc gtcccgacca ctcccccaga gatcgccaag tctttggaat    1620
taatcgcctc ccaaccacag aaaccagaag actccaaaaa gaa                      1663

<210> SEQ ID NO 5
<211> LENGTH: 1324
<212> TYPE: DNA
<213> ORGANISM: Diuraphis noxia

<400> SEQUENCE: 5
catcccaaca tacggcaatt ttctgatcac ggtatacgtc aaaaaaatc accatgaaca       60 ctttggtgag ttaaataata tttctttaaa tcttcttaaa aaagacatag caatattatc     120
attttatttt ttaatttagt tatacaacgc attgtataat agtttcaatt tataaacagt     180 ttaaatttt agtttcaatt taaaattgac attcacctg taaaagtttt cacagtatat      240
cttcacagca aaaatatgc ataaaattat ttcttdcatg atttcacagc aaaaaatatg     300
cataaaatta tttctttcct cagcacttta tacaattttc gtgccttcgt ttttaggtag    360
tgttagtagc tgtcatcgca gcggtgtctg ctgcggcccc acctcaggaa gctgccaaag    420
cttttacttt cagtggattc ccatccaacc aagcctacta cccaggccaa caagggtact    480
acccaggata cattggttac cagggttatc aaggttacag cggattccgt aatggatact    540
acccgggaca caaggatac tacccaggat accaaggtta ccagggatac tacccaggat     600
accaaggtta ccagggatac tacccaggat atcaaggttt aatttcgtta attatacgtc    660
taaaacactg cagagtcaca tgatgtgtta aagtttctt ataatttact attttcacat     720
aggttacaac cgcggttact acccaggtgc cccagccgtc taccccaccg tcaccccgc     780 cccaatcatc gcaccagtgc cagtcgcgcc caaggctgtt tctccagtgt acaaacccgt    840
agacaacaaa gtgccagcta ccttaaaca atcgcaagaa gctgacttga acggattcaa    900
atacgggtta gtattataat tggtacatta ttattcgatc ggttttctgc atcacagcga    960
atggtggatt aaaattgaga aatagagacc cgcgccaaat ggcatgtcca caaaaaatac   1020
attgtttgta ataacggat atatttgtgt gcattttcag atacgaaacc gaaaacggca   1080
tcgtcgccca ggctgctgga tacgttaaga acgccggttc cgaaaacgcc gtccaagtga   1140
tcgaaggctc gtatgcctac atcggtgacg atggtgctcc agtcgaagtc aagtactacg   1200
ctgacgagac cggttaccac gcagccgaa acgtcgtccc gaccactccc ccagagatcg    1260
ccaagtcttt ggaattaatc gcctcccaac cacagaaacc agaagactcc aaaagaagt   1320 aaac                                                                1324

<210> SEQ ID NO 6
<211> LENGTH: 1664
<212> TYPE: DNA
<213> ORGANISM: Diuraphis noxia

<400> SEQUENCE: 6
cggtatacgt ccaaaaaaat caccatgaac actttggtga gttaaataat atttctttaa     60
atcttcttaa aaaagacata gcaatattat catttttattt tttaatttag ttatacaacg   120
cattgtataa tagtttcaat tttataaacag tttaatttaa agaaaaaata gtatarttac   180
tgaaattatt tattattttc gtactttatc atacacttat gaatttttag tatttttggt    240
```

```
atacgagaat atcttattat tttataaata tcttataaaa taaatgct

<222> LOCATION: (4143)..(4143)
<223> OTHER INFORMATION: n is a, c, g, or t
<220> FEATURE:
<221> NAME/KEY: misc_feature
<222> LOCATION: (4173)..(4174)
<223> OTHER INFORMATION: n is a, c, g, or t

<400> SEQUENCE: 7

| | | | | | |
|---|---|---|---|---|---|
| catcccaaca | tacggcaatt | ttctgatcac | ggtatacgtc | caaaaaaatc | accatgaaca | 60 |
| ctttggtgag | ttaaataata | tttctttaaa | tcttcttaaa | aaagacatag | caatattatc | 120 |
| attttatttt | ttaatttagt | tatacaacgc | attgtataat | agtttcaatt | tataaacagt | 180 |
| ttaatttaaa | gaaaaaatag | tatarttact | gaaattattt | attattttcg | tactttatca | 240 |
| tacacttatg | aattttagt | attttggta | tacgagaata | tcttattatt | ttataaatat | 300 |
| cttataaaat | aaatgctcat | attatgttat | acttatttt | taaattaatg | aaactacgaa | 360 |
| aaaattaatt | ttaactcaaa | ttttcaaatt | ttttaagttc | aaataagtac | ctcaatttat | 420 |
| attatgaaca | gtgtaaaagt | ataatattta | cgtttactgc | aaccattatt | atattagaat | 480 |
| cagtcttatt | attttgtac | ttcataaaaa | aatgcctgaa | aattaaaatt | taaaagatat | 540 |
| ctctacaatt | taacgcatag | gtaatcttat | taatcgtaat | catatttaa | ccaaatccat | 600 |
| atttttagtt | tcaatttaaa | attgacatta | cacctgtaaa | agttttcaca | gtatatcttc | 660 |
| acagcaaaaa | atatgcataa | aattatttct | ttcctcagca | ctttatacaa | ttttcgtgcc | 720 |
| ttcgttttta | ggtagtgtta | gtagctgtca | tcgcagcggt | gtctgctgcg | gccccacctc | 780 |
| aggaagctgc | caaagctttt | actttcagtg | gattcccatc | caaccaagcc | tactacccag | 840 |
| gccaacaagg | gtactaccca | ggatacattg | gttaccagkg | ttatcaaggt | tacagcggat | 900 |
| tccgtaatgg | atactacccg | ggacaacaag | gatactaccc | aggataccaa | ggttaccagg | 960 |
| gatactaccc | aggataccaa | ggttaccagg | gatactaccc | aggatatcaa | ggtttaattt | 1020 |
| cgttaattat | acgtctaaaa | cactgcagag | tcacatgatg | tgttataagt | ttcttataat | 1080 |
| ttactatttt | cacataggtt | acaaccgcgg | ttactaccca | ggtgcccag | ccgtctaccc | 1140 |
| caccgtcacc | cccgccccaa | tcatcgcacc | agtgccagtc | gcgcccaagg | ctgtttctcc | 1200 |
| agtgtacaaa | cccgtagaca | acaaagtgcc | agctatcctt | aaacaatcgc | aagaagctga | 1260 |
| cttgaacgga | ttcaaatacg | ggttagtatt | ataattggta | cattattatt | cgatcggttt | 1320 |
| tctgcatcac | agcgaatggt | ggattaaaat | tgagaaatag | agacccgcgc | caaatggcat | 1380 |
| gtccacaaaa | aatacattgt | ttgtaaataa | cggatatatt | tgtgtgcatt | ttcagatacg | 1440 |
| aaaccgaaaa | cggcatcgtc | gcccaggctg | ctggatacgt | taagaacgcc | ggttccgaaa | 1500 |
| acgccgtcca | agtgatcgaa | ggctcgtatg | cctacatcgg | tgacgatggt | gctccagtcg | 1560 |
| aagtcaagta | ctacgctgac | gagaccggtt | accacgcagc | cggaaacgtc | gtcccgacca | 1620 |
| ctccccccaga | gatcgccaag | tctttggaat | taatcgcctc | ccaaccacag | aaaccagaag | 1680 |
| actccaaaaa | gaagtaaacc | cagctcgcat | gtaaccatca | tgtacgctga | aacgccccaa | 1740 |
| acactcgtat | accattagct | attagatacc | gcatgtgaaa | tcatgcatat | ttttatcatt | 1800 |
| gcaaatattg | tgtacctatg | cagtgatttt | cgttattcgt | atctgaacga | cgaatatcga | 1860 |
| cacatttact | gtacatagta | attccagttat | aatatgttgg | atgtaacaaa | aaagatgaa | 1920 |
| aatataaaaa | cttgaagtta | aatatcgtac | aatgttttct | tattccactc | gttagtcggt | 1980 |
| ctttaagtcc | atgcgtcatg | catctatgtt | atccttctagc | aaaaatatat | tctacaagtt | 2040 |
| acaaactatg | tagataacat | aatngntatt | atgtgttatg | tttagtaaca | gttcgatttc | 2100 |

```
ggcaccatct gcccgtttga atgtgtgatt gtccgaaacg tcatgttact tgcaagtaag    2160
taataagcca tagcttattt ttgtgtttta tctaatttga ggtatatcag gatacaatgc    2220
taaaaactgc attgaaatca aaaataaag aatnaatatc gatgttaata attgtaccta    2280
catacgattt cttattgtta tattatgttw ataaaaagtc aatgatacac atttataag    2340 attgtccata cttctttcat tataatttta tgctctacac atatcaatca tattattttt    2400
aatttttttt tgcaaatcaa catacatttt tttccgggag ttatcaattt atctttgcct    2460
aatttaacta actmataaaa attaattagc tgatttattc gtatggcata ttttgacaca    2520
taatatacat aaaaagttgt aacacggaat aaaataagaa taananaata gaataaaata    2580
aaataaaaaa atccatataa naaaatattt ctaaattgtt taattgtctt atttaataa    2640 tgtgtgggga gaatggtggt agcctgcacg tggccctccc tgcatgcgct tgtagatttc    2700
ctgaagaccc ttgtgtacga agacagacta cgagcgtatc taatatcacc accaaagtgc    2760
tgatacccag caacgacac agtaatatgc agcctttaaa cggcccttt cagggcgatt    2820 caacgcagat attaggccca tgccttagga tatgtcacct aaatattgaa ggtatttcgt    2880
cagctaagag tgaaattcta tctaaactta tgagagagaa aaaagttgat gttattgcac    2940
tcaaggaaat taaatgacgc aataacaatg tttatagttt tatgctattt tacagtagta    3000
attttgtaga tattgacact aaaacagagc gtgccgcgta attatctgca aattaatgtt    3060
agcgaagctg gaataatcat ctccaaaaaa agaaaaagat tatctcttga atgactcaat    3120
ctaatattat tgctgcattc atatttcaaa tcaaattaaa attctgaaac gttgatggaa    3180
aaactactgg aagaagaaaa ttcgtaaatt gmtactcaat gaatactttt cagttagtac    3240
aaaataattt ataattgata attaatttac actcataata tactgtctct tatacacatc    3300
tagatgtgta taagagacag gattgggatc caattaata gtgcctaata aaaattataa    3360 aaacaaaat aaattactt ttacaatcga tcgtaataat tgttatttta ttttgtttac    3420
ttaaactggc actttgacca aaaatataaa acctgtttgt taaatacatg ttattttggt    3480
accatcaaat gaaaaaaact tgcgtgttta gtaaattat ttcatagatc actctaatat    3540
tatttatgag ttatgtaaaa tacatgatgc aaatatcaaat gatttttttt ttttatatt    3600 aagcctcggc gtcaaaggcc attgrtggaa acaataaatt agaggtaaaa catatttat    3660 tatacattta attttagttg tattgttacc aattttacca taaatcataa tagccaatta    3720
taaattataa tgaccacata taaaatgaat taggtattta aatttgaatg aggttccagt    3780
tataaccaaa aaaaaaaaaa tcacgcaaca gccgacaagt aagttatcgt gtatgaatat    3840
tawwcaagta agtaatttgt aatttatata atttatata aakagwtarc gtttaaatac    3900
ataattgtat aaacgagtat tatataggaa ggtgtatatt atacgatatt ttacaaacat    3960
cttttatagt cgatacaata taatagtagt attatgattt tataatttta aattcacttc    4020
cacagaagta aaaactgcta tattaagatt tatcaataaa taatgataca gttcaattaa    4080
attatgtata ttgtaataag tattttgttt tcattttgaa aggcttttaa tatatatata    4140
tantgtataa atttttttt ttktrattt tannaatata attgtattta tttatac       4197
```

<210> SEQ ID NO 8
<211> LENGTH: 18
<212> TYPE: DNA
<213> ORGANISM: Diuraphis noxia

<400> SEQUENCE: 8

```
cccatccaac caagccta                                                  18
```

<210> SEQ ID NO 9
<211> LENGTH: 20
<212> TYPE: DNA
<213> ORGANISM: Diuraphis noxia

<400> SEQUENCE: 9
ccgggacaac aaggatacta                                               20

<210> SEQ ID NO 10
<211> LENGTH: 20
<212> TYPE: DNA
<213> ORGANISM: Diuraphis noxia

<400> SEQUENCE: 10
tagtatcctt gttgtcccgg                                               20

<210> SEQ ID NO 11
<211> LENGTH: 20
<212> TYPE: DNA
<213> ORGANISM: Diuraphis noxia

<400> SEQUENCE: 11
gtagacaaca aagtgccagc                                               20

<210> SEQ ID NO 12
<211> LENGTH: 20
<212> TYPE: DNA
<213> ORGANISM: Diuraphis noxia

<400> SEQUENCE: 12
aattaatcgc ctcccaacca                                               20

<210> SEQ ID NO 13
<211> LENGTH: 20
<212> TYPE: DNA
<213> ORGANISM: Diuraphis noxia

<400> SEQUENCE: 13
tggttgggag gcgattaatt                                               20

<210> SEQ ID NO 14
<211> LENGTH: 20
<212> TYPE: DNA
<213> ORGANISM: Diuraphis noxia

<400> SEQUENCE: 14
aaaacgccgt ccaagtgatc                                               20

<210> SEQ ID NO 15
<211> LENGTH: 20
<212> TYPE: DNA
<213> ORGANISM: Diuraphis noxia

<400> SEQUENCE: 15
ggtgctccag tcgaagtcaa                                               20

<210> SEQ ID NO 16
<211> LENGTH: 20
<212> TYPE: DNA
<213> ORGANISM: Diuraphis noxia

<400> SEQUENCE: 16

-continued

```
ttgacttcga ctggagcacc                                                    20
```

<210> SEQ ID NO 17
<211> LENGTH: 243
<212> TYPE: PRT
<213> ORGANISM: Diuraphis noxia
<220> FEATURE:
<221> NAME/KEY: MISC_FEATURE
<222> LOCATION: (54)..(54)
<220> FEATURE:
<221> NAME/KEY: MISC_FEATURE
<222> LOCATION: (54)..(54)
<223> OTHER INFORMATION: X = G or C

<400> SEQUENCE: 17

Met Asn Thr Leu Val Val Leu Val Ala Val Ile Ala Ala Val Ser Ala
1               5                   10                  15

Ala Ala Pro Pro Gln Glu Ala Ala Lys Ala Phe Thr Phe Ser Gly Phe
            20                  25                  30

Pro Ser Asn Gln Ala Tyr Tyr Pro Gly Gln Gln Gly Tyr Tyr Pro Gly
        35                  40                  45

Tyr Ile Gly Tyr Gln Xaa Tyr Gln Gly Tyr Ser Gly Phe Arg Gly Tyr
    50                  55                  60

Tyr Pro Gly Gln Gln Gly Tyr Tyr Pro Gly Tyr Gln Gly Tyr Gln Gly
65                  70                  75                  80

Tyr Tyr Pro Gly Tyr Gln Gly Tyr Gln Gly Tyr Tyr Pro Gly Tyr Gln
                85                  90                  95

Gly Tyr Asn Arg Gly Tyr Tyr Pro Gly Ala Pro Ala Val Tyr Pro Thr
            100                 105                 110

Val Thr Pro Ala Pro Ile Ile Ala Pro Val Pro Val Ala Pro Lys Ala
        115                 120                 125

Val Ser Pro Val Tyr Lys Pro Val Asp Asn Lys Val Pro Ala Ile Leu
    130                 135                 140

Lys Gln Ser Gln Glu Ala Asp Leu Asn Gly Phe Lys Tyr Gly Tyr Glu
145                 150                 155                 160

Thr Glu Asn Gly Ile Val Ala Gln Ala Ala Gly Tyr Val Lys Asn Ala
                165                 170                 175

Gly Ser Glu Asn Ala Val Gln Val Ile Glu Gly Ser Tyr Ala Tyr Ile
            180                 185                 190

Gly Asp Asp Gly Ala Pro Val Glu Val Lys Tyr Tyr Ala Asp Glu Thr
        195                 200                 205

Gly Tyr His Ala Ala Gly Asn Val Val Pro Thr Thr Pro Pro Glu Ile
    210                 215                 220

Ala Lys Ser Leu Glu Leu Ile Ala Ser Gln Pro Gln Lys Pro Glu Asp
225                 230                 235                 240

Ser Lys Lys

<210> SEQ ID NO 18
<211> LENGTH: 243
<212> TYPE: PRT
<213> ORGANISM: Diuraphis noxia

<400> SEQUENCE: 18

Met Asn Thr Leu Val Val Leu Val Ala Val Ile Ala Ala Val Ser Ala
1               5                   10                  15

Ala Ala Pro Pro Gln Glu Ala Ala Lys Ala Phe Thr Phe Ser Gly Phe
            20                  25                  30

Pro Ser Asn Gln Ala Tyr Tyr Pro Gly Gln Gln Gly Tyr Tyr Pro Gly

```
                35                  40                  45
Tyr Ile Gly Tyr Gln Cys Tyr Gln Gly Tyr Ser Gly Phe Arg Gly Tyr
 50                  55                  60

Tyr Pro Gly Gln Gln Gly Tyr Tyr Pro Gly Tyr Gln Gly Tyr Gln Gly
 65                  70                  75                  80

Tyr Tyr Pro Gly Tyr Gln Gly Tyr Gln Gly Tyr Tyr Pro Gly Tyr Gln
                85                  90                  95

Gly Tyr Asn Arg Gly Tyr Tyr Pro Gly Ala Pro Ala Val Tyr Pro Thr
                100                 105                 110

Val Thr Pro Ala Pro Ile Ile Ala Pro Val Pro Val Ala Pro Lys Ala
            115                 120                 125

Val Ser Pro Val Tyr Lys Pro Val Asp Asn Lys Val Pro Ala Ile Leu
            130                 135                 140

Lys Gln Ser Gln Glu Ala Asp Leu Asn Gly Phe Lys Tyr Gly Tyr Glu
145                 150                 155                 160

Thr Glu Asn Gly Ile Val Ala Gln Ala Ala Gly Tyr Val Lys Asn Ala
                165                 170                 175

Gly Ser Glu Asn Ala Val Gln Val Ile Glu Gly Ser Tyr Ala Tyr Ile
            180                 185                 190

Gly Asp Asp Gly Ala Pro Val Glu Val Lys Tyr Tyr Ala Asp Glu Thr
            195                 200                 205

Gly Tyr His Ala Ala Gly Asn Val Val Pro Thr Thr Pro Pro Glu Ile
            210                 215                 220

Ala Lys Ser Leu Glu Leu Ile Ala Ser Gln Pro Gln Lys Pro Glu Asp
225                 230                 235                 240

Ser Lys Lys

<210> SEQ ID NO 19
<211> LENGTH: 243
<212> TYPE: PRT
<213> ORGANISM: Diuraphis noxia

<400> SEQUENCE: 19

Met Asn Thr Leu Val Val Leu Val Ala Val Ile Ala Ala Val Ser Ala
1               5                   10                  15

Ala Ala Pro Pro Gln Glu Ala Ala Lys Ala Phe Thr Phe Ser Gly Phe
                20                  25                  30

Pro Ser Asn Gln Ala Tyr Tyr Pro Gly Gln Gln Gly Tyr Tyr Pro Gly
            35                  40                  45

Tyr Ile Gly Tyr Gln Gly Tyr Gln Gly Tyr Ser Gly Phe Arg Gly Tyr
 50                  55                  60

Tyr Pro Gly Gln Gln Gly Tyr Tyr Pro Gly Tyr Gln Gly Tyr Gln Gly
 65                  70                  75                  80

Tyr Tyr Pro Gly Tyr Gln Gly Tyr Gln Gly Tyr Tyr Pro Gly Tyr Gln
                85                  90                  95

Gly Tyr Asn Arg Gly Tyr Tyr Pro Gly Ala Pro Ala Val Tyr Pro Thr
                100                 105                 110

Val Thr Pro Ala Pro Ile Ile Ala Pro Val Pro Val Ala Pro Lys Ala
            115                 120                 125

Val Ser Pro Val Tyr Lys Pro Val Asp Asn Lys Val Pro Ala Ile Leu
            130                 135                 140

Lys Gln Ser Gln Glu Ala Asp Leu Asn Gly Phe Lys Tyr Gly Tyr Glu
145                 150                 155                 160

Thr Glu Asn Gly Ile Val Ala Gln Ala Ala Gly Tyr Val Lys Asn Ala
```

```
                165                 170                 175
Gly Ser Glu Asn Ala Val Gln Val Ile Glu Gly Ser Tyr Ala Tyr Ile
            180                 185                 190

Gly Asp Asp Gly Ala Pro Val Glu Val Lys Tyr Tyr Ala Asp Glu Thr
            195                 200                 205

Gly Tyr His Ala Ala Gly Asn Val Val Pro Thr Thr Pro Pro Glu Ile
            210                 215                 220

Ala Lys Ser Leu Glu Leu Ile Ala Ser Gln Pro Gln Lys Pro Glu Asp
225                 230                 235                 240

Ser Lys Lys
```

```
<210> SEQ ID NO 20
<211> LENGTH: 718
<212> TYPE: DNA
<213> ORGANISM: Diuraphis noxia

<400> SEQUENCE: 20
tccaaaaaaa tcaccatgaa cactttggta gtgttagtag ctgtcatcgc agcggtgtct      60
gctgcggccc cacctcagga agctgccaaa gcttttactt tcagtggatt cccatccaac    120
caagcctact acccaggcca acaagggtac tacccaggat acattggtta cagggttay    180 caaggttaca gcggattccg taatggatac tacccgggac aacaaggata ctacccagga    240
taccaaggtt accagggata ctacccagga taccaaggtt accagggata ctacccagga    300
tatcaaggtt acaaccgcgg ttactaccca ggtgccccag ccgtctaccc caccgtcacc    360
cccgccccaa tcatcgcacc agtgccagtc gcgcccaagg ctgtttctcc agtgtacaaa    420
cccgtagaca caaagtgcc agctatcctt aaacaatcgc aagaagctga cttgaacgga    480
ttcaaatacg gatacgaaac cgaaaacggc atcgtcgccc aggctgctgg atacgttaag    540
aacgccggtt ccgaaaacgc cgtccaagtg atcgaaggct cgtatgccta catcggtgac    600
gatggtgctc cagtcgaagt caagtactac gctgacgaga ccggttacca cgcagccgga    660
aacgtcgtcc cgaccactcc cccagagatc gccaagtctt tggaattaat cgcctccc      718
```

```
<210> SEQ ID NO 21
<211> LENGTH: 826
<212> TYPE: DNA
<213> ORGANISM: Diuraphis noxia

<400> SEQUENCE: 21
catcccaaca tacggcaatt ttctgatcac ggtatacgtc caaaaaaatc accatgaaca      60
ctttggtagt gttagtagct gtcatcgcag cggtgtctgc tgcggcccca cctcaggaag    120
ctgccaaagc ttttactttc agtggattcc catccaacca agcctactac ccaggccaac    180
aagggtacta cccaggatac attggttacc agggttatca aggttacagc ggattccgta    240
atggatacta cccgggacaa caaggatact acccaggata ccaaggttac cagggatact    300
acccaggata ccaaggttac cagggatact acccaggata tcaaggttac aaccgcggtt    360
actacccagg tgccccagcc gtctacccca ccgtcacccc cgccccaatc atcgcaccag    420
tgccagtcgc gcccaaggct gtttctccag tgtacaaacc cgtagacaac aaagtgccag    480
ctatccttaa caatcgcaa gaagctgact tgaacggatt caaatacgga tacgaaaccg    540
aaaacggcat cgtcgcccag gctgctggat acgttaagaa cgccggttcc gaaaacgccg    600
tccaagtgat cgaaggctcg tatgcctaca tcggtgacga tggtgctcca gtcgaagtca    660
agtactacgc tgacgagacc ggttaccacg cagccggaaa cgtcgtcccg accactcccc    720
```

| cagagatcgc caagtctttg gaattaatcg cctcccaacc acagaaacca gaagactcca | 780 |
| aaaagaaatc actctaatat tatttatgag ttatgtaaaa tacatg | 826 |

<210> SEQ ID NO 22
<211> LENGTH: 730
<212> TYPE: DNA
<213> ORGANISM: Diuraphis noxia

<400> SEQUENCE: 22

| tccaaaaaaa tcaccatgaa cactttggta gtgttagtag ctgtcatcgc agcggtgtct | 60 |
| gctgcggccc cacctcagga agctgccaaa gcttttactt tcagtggatt cccatccaac | 120 |
| caagcctact acccaggcca acaagggtac tacccaggat acattggtta ccagggttay | 180 |
| caaggttaca gcggattccg taatggatac tacccgggac aacaaggata ctacccagga | 240 |
| taccaaggtt accagggata ctacccagga taccaaggtt accagggata ctacccagga | 300 |
| tatcaaggtt acaaccgcgg ttactaccca ggtgccccag ccgtctaccc caccgtcacc | 360 |
| cccgccccaa tcatcgcacc agtgccagtc gcgcccaagg ctgtttctcc agtgtacaaa | 420 |
| cccgtagaca caaagtgcc agctatcctt aaacaatcgc aagaagctga cttgaacgga | 480 |
| ttcaaatacg gatacgaaac cgaaaacggc atcgtcgccc aggctgctgg atacgttaag | 540 |
| aacgccggtt ccgaaaacgc cgtccaagtg atcgaaggct cgtatgccta catcggtgac | 600 |
| gatggtgctc cagtcgaagt caagtactac gctgacgaga ccggttacca cgcagccgga | 660 |
| aacgtcgtcc cgaccactcc cccagagatc gccaagtctt tggaattaat cgcctcccaa | 720 |
| ccacagaaac | 730 |

<210> SEQ ID NO 23
<211> LENGTH: 1457
<212> TYPE: RNA
<213> ORGANISM: Diuraphis noxia
<220> FEATURE:
<221> NAME/KEY: misc_feature
<222> LOCATION: (1403)..(1403)
<223> OTHER INFORMATION: n is a, c, g, or u
<220> FEATURE:
<221> NAME/KEY: misc_feature
<222> LOCATION: (1433)..(1434)
<223> OTHER INFORMATION: n is a, c, g, or u

<400> SEQUENCE: 23

| caucccaaca uacggcaauu uucugaucac gguauacguc caaaaaaauc accaugaaca | 60 |
| cuuugguagu guuaguagcu gucaucgcag cggugucugc ugcggcccca ccucaggaag | 120 |
| cugccaaagc uuuuacuuuc aguggauucc cauccaacca agccuacuac ccaggccaac | 180 |
| aagguacua cccaggauac auugguuacc aggguuayca agguuacagc ggauccgua | 240 |
| auggauacua cccgggacaa caaggauacu acccaggaua ccaagguuac cagggauacu | 300 |
| acccaggaua ccaagguuac cagggauacu acccaggaua ucaagguuac aaccgcgguu | 360 |
| acuacccagg ugccccagcc gucuacccca cgucacccc cgcccaauc aucgcaccag | 420 |
| ugccagucgc gcccaaggcu guuucuccag uguacaaacc guagacaac aaagugccag | 480 |
| cuauccuuaa acaaucgcaa gaagcugacu ugaacggauu caaauacgga uacgaaaccg | 540 |
| aaaacggcau cgucgcccag gcugcuggau acguuaagaa cgccgguucc gaaaacgccg | 600 |
| uccaagugau cgaaggcucg uaugccuaca ucggugacga uggugcucca gucgaaguca | 660 |
| aguacuacgc ugacgagacc gguuaccacg cagccggaaa cgucguccg accacucccc | 720 |

| | |
|---|---|
| cagagaucgc caagucuuug gaauuaaucg ccucccaacc acagaaacca gaagacucca | 780 |
| aaaagaaauc acucuaauau uauuuaugag uuauguaaaa uacaugaugc aauaucaaau | 840 |
| gauuuuuuuu uuuuuauauu aagccucggc gucaaaggcc auugruggaa acaauaaauu | 900 |
| agagguaaaa cauauuuuau uauacauuua auuuaguug uauuguuacc aauuuuacca | 960 |
| uaaaucauaa uagccaauua uaaauuauaa ugaccacaua uaaaaugaau uagguauuua | 1020 |
| aauuugaaug agguuccagu uauaaccaaa aaaaaaaaaa ucacgcaaca gccgacaagu | 1080 |
| aaguuaucgu guaugaauau uawwcaagua aguaauuugu aauuuauaua auuuuauaua | 1140 |
| aakagwuarc guuuaaauac auaauugau aaacgaguau uauauaggaa gguguauauu | 1200 |
| auacgauauu uuacaaacau cuuuuauagu cgauacaaua uaauaguagu auuaugauuu | 1260 |
| uauaauuuua aauucacuuc cacagaagua aaaacugcua uauuaagauu uaucaauaaa | 1320 |
| uaaugauaca guucaauuaa auuauguaua uuguauaag uauuuuguuu ucauuugaa | 1380 |
| aggcuuuuaa uauauauaua uanuguauaa auuuuuuuuu uukurauuuu uannaauaua | 1440 |
| auuguauuua uuuauac | 1457 |

<210> SEQ ID NO 24
<211> LENGTH: 744
<212> TYPE: DNA
<213> ORGANISM: Diuraphis noxia

<400> SEQUENCE: 24

| | |
|---|---|
| atgaacacuu tggtagtgtt agtagctgtc atcgcagcgg tgtctgctgc ggccccacct | 60 |
| caggaagctg ccaaagcttt tactttcagt ggattcccat ccaaccaagc ctactaccca | 120 |
| ggccaacaag ggtactaccc aggatacatt ggttaccagg ttatcaagg ttacagcgga | 180 |
| ttccgtaatg gatactaccc gggacaacaa ggatactacc caggatacca aggttaccag | 240 |
| ggatactacc caggatacca aggttaccag ggatactacc caggatatca aggttacaac | 300 |
| cgcggttact acccaggtgc cccagccgtc taccccaccg tcaccccgc cccaatcatc | 360 |
| gcaccagtgc cagtcgcgcc caaggctgtt tctccagtgt acaaacccgt agacaacaaa | 420 |
| gtgccagcta tccttaaaca atcgcaagaa gctgacttga acggattcaa atacggatac | 480 |
| gaaaccgaaa acggcatcgt cgcccaggct gctggatacg ttaagaacgc cggttccgaa | 540 |
| aacgccgtcc aagtgatcga aggctcgtat gcctacatcg tgacgatgg tgctccagtc | 600 |
| gaagtcaagt actacgctga cgagaccggt taccacgcag ccggaaacgt cgtcccgacc | 660 |
| actcccccag atcgccaa gtctttggaa ttaatcgcct cccaaccaca gaaaccagaa | 720 |
| gactccaaaa agaaatcact ctaa | 744 |

<210> SEQ ID NO 25
<211> LENGTH: 1664
<212> TYPE: DNA
<213> ORGANISM: Diuraphis noxia

<400> SEQUENCE: 25

| | |
|---|---|
| cggtatacgt ccaaaaaaat caccatgaac actttggtga gttaaataat atttctttaa | 60 |
| atcttcttaa aaaagacata gcaatattat cattttattt tttaatttag ttatacaacg | 120 |
| cattgtataa tagtttcaat ttataaacag tttaatttaa agaaaaaata gtatarttac | 180 |
| tgaaattatt tattatttc gtactttatc atacacttat gaattttag tatttttggt | 240 |
| atacgagaat atcttattat tttataaata tcttataaaa taaatgctca tattatgtta | 300 |
| tacttatttt ttaaattaat gaaactacga aaaaattaat tttaactcaa atttttcaaat | 360 |

-continued

```
tttttaagtt caaataagta cctcaatttta tattatgaac agtgtaaaag tataatattt    420
acgtttactg caaccattat tatattagaa tcagtcttat tattttttgta cttcataaaa    480 aaatgcctga aaattaaaat ttaaaagata tctctacaat ttaacgcata ggtaatctta    540
ttaatcgtaa tcatatttta accaaatcca tattttttagt ttcaatttaa aattgacatt    600
acacctgtaa aagttttcac agtatatctt cacagcaaaa aatatgcata aaattatttc    660
tttcctcagc actttataca attttcgtgc cttcgttttt aggtagtgtt agtagctgtc    720
atcgcagcgg tgtctgctgc ggccccacct caggaagctg ccaaagcttt tactttcagt    780
ggattcccat ccaaccaagc ctactaccca ggccaacaag ggtactaccc aggatacatt    840
ggttaccagk ttatcaagg ttacagcgga ttccgtaatg gatactaccc gggacaacaa     900
ggatactacc caggatacca aggttaccag ggatactacc caggatacca aggttaccag    960
ggatactacc caggatatca aggtttaatt tcgttaatta tacgtctaaa acactgcaga    1020
gtcacatgat gtgttataag tttcttataa tttactattt tcacataggt tacaaccgcg    1080
gttactaccc aggtgcccca gccgtctacc ccaccgtcac ccccgcccca atcatcgcac    1140
cagtgccagt cgcgcccaag gctgtttctc cagtgtacaa acccgtagac aacaaagtgc    1200
cagctatcct taaacaatcg caagaagctg acttgaacgg attcaaatac gggttagtat    1260
tataattggt acattattat tcgatcggtt ttctgcatca cagcgaatgg yggattaaaa    1320
ttgagaaata gagacccgcg ccaaatggca tgtccacaaa aaatacattg tttgtaaata    1380
acggatatat ttgtgtgcat tttcagatac gaaaccgaaa acggcatcgt cgcccaggct    1440
gctggatacg ttaagaacgc cggttccgaa aacgccgtcc aagtgatcga aggctcgtat    1500
gcctacatcg gtgacgatgg tgctccagtc gaagtcaagt actacgctga cgagaccggt    1560
taccacgcag ccggaaacgt cgtcccgacc actcccccag agatcgccaa gtctttggaa    1620
ttaatcgcct cccaaccaca gaaaccagaa gactccaaaa agaa                     1664
```

<210> SEQ ID NO 26
<211> LENGTH: 20
<212> TYPE: DNA
<213> ORGANISM: Diuraphis noxia

<400> SEQUENCE: 26
cccgtatgag aagccgactg                    20

<210> SEQ ID NO 27
<211> LENGTH: 20
<212> TYPE: DNA
<213> ORGANISM: Diuraphis noxia

<400> SEQUENCE: 27
ccatcttggt gggagctctg                    20

<210> SEQ ID NO 28
<211> LENGTH: 19
<212> TYPE: DNA
<213> ORGANISM: Diuraphis noxia

<400> SEQUENCE: 28
ttactaccca ggtgcccca                     19

<210> SEQ ID NO 29
<211> LENGTH: 20
<212> TYPE: DNA

```
<213> ORGANISM: Diuraphis noxia

<400> SEQUENCE: 29
ctgtggttgg gaggcgatta                                              20

<210> SEQ ID NO 30
<211> LENGTH: 23
<212> TYPE: DNA
<213> ORGANISM: Diuraphis noxia

<400> SEQUENCE: 30
gcatcagttg tgtcatttgt cca                                          23

<210> SEQ ID NO 31
<211> LENGTH: 18
<212> TYPE: DNA
<213> ORGANISM: Diuraphis noxia

<400> SEQUENCE: 31
gtttgggccg tttcagcg                                                18

<210> SEQ ID NO 32
<211> LENGTH: 27
<212> TYPE: DNA
<213> ORGANISM: Diuraphis noxia

<400> SEQUENCE: 32
tcgtacttta tcatacactt atgaatt                                      27

<210> SEQ ID NO 33
<211> LENGTH: 20
<212> TYPE: DNA
<213> ORGANISM: Diuraphis noxia

<400> SEQUENCE: 33
gcgggtctct atttctcaat                                              20

<210> SEQ ID NO 34
<211> LENGTH: 21
<212> TYPE: RNA
<213> ORGANISM: Diuraphis noxia

<400> SEQUENCE: 34
auuucagaga gacaucggag g                                            21

<210> SEQ ID NO 35
<211> LENGTH: 21
<212> TYPE: RNA
<213> ORGANISM: Diuraphis noxia

<400> SEQUENCE: 35
uccgaugucu cucugaaauu g                                            21

<210> SEQ ID NO 36
<211> LENGTH: 50
<212> TYPE: DNA
<213> ORGANISM: Diuraphis noxia

<400> SEQUENCE: 36
gtcgtatcca gtgcagggtc cgaggtattc gcactggata cgaccctccg             50

<210> SEQ ID NO 37
<211> LENGTH: 21
```

```
<212> TYPE: DNA
<213> ORGANISM: Diuraphis noxia

<400> SEQUENCE: 37 gccaccatt

-continued

```
<211> LENGTH: 21
<212> TYPE: RNA
<213> ORGANISM: Myzus persicae

<400> SEQUENCE: 45
uuuggagucu ucugguuucu g                                              21
```